US007011809B2

(12) United States Patent
Singleton et al.

(10) Patent No.: US 7,011,809 B2
(45) Date of Patent: *Mar. 14, 2006

(54) ATTRITION RESISTANT GAMMA-ALUMINA CATALYST SUPPORT

(75) Inventors: Alan H. Singleton, Baden, PA (US); Rachid Oukaci, Gibsonia, PA (US); James G. Goodwin, Cranberry Township, PA (US)

(73) Assignee: Sasol Technology (UK) Limited, Sasolburg (ZA)

( * ) Notice: Subject to any disclaimer, the term of this patent is extended or adjusted under 35 U.S.C. 154(b) by 4 days.

This patent is subject to a terminal disclaimer.

(21) Appl. No.: 10/851,379

(22) Filed: May 21, 2004

(65) Prior Publication Data

US 2004/0214904 A1 Oct. 28, 2004

Related U.S. Application Data

(60) Continuation of application No. 09/844,379, filed on Apr. 27, 2001, now Pat. No. 6,740,621, which is a division of application No. 09/316,562, filed on May 21, 1999, now Pat. No. 6,262,132.

(51) Int. Cl.
*C01F 7/02* (2006.01)
*B01J 21/00* (2006.01)

(52) U.S. Cl. .................. 423/628; 423/626; 502/355

(58) Field of Classification Search ........... 502/429, 502/355; 423/626, 628
See application file for complete search history.

(56) References Cited

U.S. PATENT DOCUMENTS

| 2,393,909 A | 1/1946 | Johnson ................. 260/449.6 |
| 2,515,245 A | 7/1950 | Mattox ..................... 252/417 |
| 2,540,109 A | 2/1951 | Friedman ................. 260/449.6 |
| 2,544,574 A | 3/1951 | Walker et al. ........... 260/449.6 |
| 2,598,186 A | 5/1952 | Mayland ........................ 257/2 |
| 2,605,234 A | 7/1952 | Friedman .................... 252/411 |
| 2,608,568 A | 8/1952 | Hogan et al. ............ 260/449.6 |
| 2,620,313 A | 12/1952 | Odell ........................ 252/417 |
| 2,632,015 A | 3/1953 | Kratzer .................... 260/449.6 |
| 2,635,110 A | 4/1953 | Watson .................... 260/449.6 |
| 2,661,338 A | 12/1953 | Lanning .................... 252/417 |
| 2,662,912 A | 12/1953 | Martin ..................... 260/449.6 |
| 2,735,802 A | 2/1956 | Jahnig ......................... 196/52 |
| 2,775,607 A | 12/1956 | Kolbel et al. ............ 260/449.6 |
| 2,852,350 A | 9/1958 | Kolbel et al. ................ 23/288 |
| 3,617,517 A | 11/1971 | Rashkin ..................... 208/136 |
| 3,669,904 A | 6/1972 | Cornelius et al. ........... 252/465 |
| 3,853,789 A | 12/1974 | Warthen et al. ............. 252/463 |

(Continued)

FOREIGN PATENT DOCUMENTS

EP  0174696  3/1986

(Continued)

OTHER PUBLICATIONS

Kogelbauer et al., Ruthenium Promotion of CO/Al$_2$O$_3$ Fischer-Tropsch Catalysts, *Journal of Catalysts*, Jan. 11, 1996, vol. 160, pp. 125-133.

(Continued)

*Primary Examiner*—Stanley S. Silverman
*Assistant Examiner*—Jonas N. Strickland
(74) *Attorney, Agent, or Firm*—Fellers, Snider, Blankenship, Bailey & Tippens, P.C.

(57) ABSTRACT

A γ-alumina catalyst support having improved attrition resistance produced by a method comprising the steps of treating a particulate γ-alumina material with an acidic aqueous solution comprising water and nitric acid and then, prior to adding any catalytic material thereto, calcining the treated γ-alumina.

5 Claims, 4 Drawing Sheets

U.S. PATENT DOCUMENTS

| | | | |
|---|---|---|---|
| 3,943,052 A | 3/1976 | Kmak et al. | 208/140 |
| 3,966,586 A | 6/1976 | Owen et al. | 208/120 |
| 3,988,263 A | 10/1976 | Hansford | 252/466 |
| 4,079,072 A | 3/1978 | Finch | 260/449 |
| 4,088,671 A | 5/1978 | Kobylinski | 260/449.6 |
| 4,089,811 A | 5/1978 | Koniz et al. | 252/463 |
| 4,090,949 A | 5/1978 | Owen et al. | 208/78 |
| 4,102,978 A | 7/1978 | Kiovsky | 423/626 |
| 4,133,841 A | 1/1979 | Cosyns et al. | 260/676 |
| 4,179,408 A | 12/1979 | Sanchez et al. | 252/448 |
| 4,207,208 A | 6/1980 | Lucki et al. | 252/455 |
| 4,208,191 A | 6/1980 | Sze | 48/210 |
| 4,218,388 A | 8/1980 | Schaper et al. | 260/449 |
| 4,219,445 A | 8/1980 | Finch | 252/443 |
| 4,235,754 A | 11/1980 | Chester | 252/455 |
| 4,252,736 A | 2/1981 | Haag et al. | 260/450 |
| 4,260,518 A | 4/1981 | Katzer et al. | 252/411 |
| 4,279,830 A | 7/1981 | Haag et al. | 518/700 |
| 4,315,839 A | 2/1982 | Bouge et al. | 252/448 |
| 4,379,134 A | 4/1983 | Weber et al. | 423/626 |
| 4,385,193 A | 5/1983 | Bijwaard et al. | 585/310 |
| 4,403,044 A | 9/1983 | Post et al. | 518/714 |
| 4,423,265 A | 12/1983 | Chu et al. | 585/322 |
| 4,433,065 A | 2/1984 | van der Burgt et al. | 518/703 |
| 4,476,245 A | 10/1984 | Siefert | 502/302 |
| 4,477,595 A | 10/1984 | Madon | 518/715 |
| 4,493,905 A | 1/1985 | Beuther et al. | 502/325 |
| 4,499,209 A | 2/1985 | Hoek et al. | 518/707 |
| 4,507,400 A | 3/1985 | Miller et al. | 502/63 |
| 4,523,047 A | 6/1985 | Chester et al. | 585/322 |
| 4,548,912 A | 10/1985 | Hettinger et al. | 502/68 |
| 4,565,831 A | 1/1986 | Wright et al. | 518/700 |
| 4,567,205 A | 1/1986 | Acuri et al. | 518/715 |
| 4,585,798 A | 4/1986 | Beuther et al. | 518/715 |
| 4,595,703 A | 6/1986 | Payne et al. | 518/715 |
| 4,605,676 A | 8/1986 | Kobylinski et al. | 518/700 |
| 4,605,678 A | 8/1986 | Brennan et al. | 518/700 |
| 4,606,811 A | 8/1986 | Hettinger | 208/108 |
| 4,619,910 A | 10/1986 | Dyer et al. | 502/336 |
| 4,637,993 A | 1/1987 | van Erp et al. | 502/242 |
| 4,663,305 A | 5/1987 | Mauldin et al. | 502/304 |
| 4,670,472 A | 6/1987 | Dyer et al. | 518/700 |
| 4,673,993 A | 6/1987 | McCaughey | 360/79 |
| 4,681,867 A | 7/1987 | Dyer et al. | 502/242 |
| 4,684,756 A | 8/1987 | Derr, Jr. et al. | 585/330 |
| 4,686,313 A | 8/1987 | Bell et al. | 585/327 |
| 4,717,702 A | 1/1988 | Beuther et al. | 502/303 |
| 4,729,981 A | 3/1988 | Kobylinski et al. | 502/259 |
| 4,738,939 A | 4/1988 | Boyle | 502/37 |
| 4,788,222 A | 11/1988 | Rice et al. | 518/700 |
| 4,801,573 A | 1/1989 | Eri et al. | 502/302 |
| 4,801,620 A | 1/1989 | Fujitani et al. | 518/715 |
| 4,822,824 A | 4/1989 | Iglesia et al. | 518/709 |
| 4,863,890 A | 9/1989 | Koll | 502/230 |
| 4,872,970 A | 10/1989 | Boyle | 208/140 |
| 4,874,732 A | 10/1989 | Miller et al. | 502/74 |
| 4,880,763 A | 11/1989 | Eri et al. | 502/302 |
| 4,908,341 A | 3/1990 | Pruden et al. | 502/30 |
| 4,910,227 A | 3/1990 | Brown et al. | 518/700 |
| 4,978,689 A | 12/1990 | Bell et al. | 518/709 |
| 4,992,406 A | 2/1991 | Mauldin et al. | 502/304 |
| 5,023,277 A | 6/1991 | McAteer | 518/715 |
| 5,028,634 A | 7/1991 | Fiato | 518/707 |
| 5,036,032 A | 7/1991 | Iglesia et al. | 502/260 |
| 5,037,791 A | 8/1991 | Comolli et al. | 502/185 |
| 5,070,064 A | 12/1991 | Hsu et al. | 502/325 |
| 5,102,851 A | 4/1992 | Eri et al. | 502/302 |
| 5,102,852 A | 4/1992 | Hung et al. | 502/314 |
| 5,116,800 A | 5/1992 | Williamson et al. | 502/303 |
| 5,140,050 A | 8/1992 | Mauldin et al. | 518/715 |
| 5,157,054 A | 10/1992 | Herbolzheimer et al. | 518/700 |
| 5,162,284 A | 11/1992 | Soled et al. | 502/324 |
| 5,206,202 A | 4/1993 | Lachman et al. | 502/216 |
| 5,248,701 A | 9/1993 | Soled et al. | 518/700 |
| 5,252,613 A | 10/1993 | Chang et al. | 518/700 |
| 5,258,411 A | 11/1993 | Behrmann et al. | 518/715 |
| 5,260,239 A | 11/1993 | Hsis | 502/30 |
| 5,268,344 A | 12/1993 | Pedrick et al. | 502/30 |
| 5,283,216 A | 2/1994 | Mitchell | 502/30 |
| 5,288,673 A | 2/1994 | Behrmann et al. | 502/30 |
| 5,292,705 A | 3/1994 | Mitchell | 502/325 |
| 5,324,335 A | 6/1994 | Benham et al. | 44/452 |
| 5,334,570 A | 8/1994 | Beauseigneur et al. | 502/304 |
| 5,348,982 A | 9/1994 | Herbolzheimer et al. | 518/700 |
| 5,356,845 A | 10/1994 | Clavenna et al. | 502/21 |
| 5,382,748 A | 1/1995 | Behrmann et al. | 585/899 |
| 5,384,336 A | 1/1995 | Koros | 518/700 |
| 5,389,690 A | 2/1995 | Mitchell | 518/700 |
| 5,407,644 A | 4/1995 | Rytter et al. | 422/147 |
| 5,411,927 A | 5/1995 | Choudhary et al. | 502/302 |
| 5,422,375 A | 6/1995 | Rytter et al. | 518/700 |
| 5,424,264 A | 6/1995 | Richard et al. | 502/261 |
| 5,430,219 A | 7/1995 | Sanflippo et al. | 585/659 |
| 5,461,022 A | 10/1995 | Dosch et al. | 502/242 |
| 5,484,757 A | 1/1996 | Szymanski et al. | 502/439 |
| 5,498,638 A | 3/1996 | Long | 518/706 |
| 5,500,449 A | 3/1996 | Benham et al. | 518/700 |
| 5,504,118 A | 4/1996 | Benham et al. | 518/719 |
| 5,506,272 A | 4/1996 | Benham et al. | 518/719 |
| 5,520,890 A | 5/1996 | Lorentzen et al. | 422/197 |
| 5,527,473 A | 6/1996 | Ackerman | 210/767 |
| 5,639,798 A | 6/1997 | Wilson et al. | 518/714 |
| 5,648,312 A | 7/1997 | Rivas et al. | 502/325 |
| 5,677,257 A | 10/1997 | Rivas et al. | 502/178 |
| 5,710,093 A | 1/1998 | Rivas et al. | 502/439 |
| 5,780,381 A | 7/1998 | Wilson et al. | 502/308 |
| 5,939,350 A | 8/1999 | Singleton et al. | 502/230 |
| 6,066,308 A | 5/2000 | Dupin et al. | 423/659 |
| 6,100,304 A | 8/2000 | Singleton et al. | 518/715 |
| 6,117,814 A | 9/2000 | Plecha et al. | 502/325 |
| 6,262,132 B1 | 7/2001 | Singleton et al. | 518/715 |
| 6,365,544 B1 | 4/2002 | Herron et al. | 502/326 |
| 6,740,621 B1 * | 5/2004 | Singleton et al. | 502/429 |

FOREIGN PATENT DOCUMENTS

| | | |
|---|---|---|
| EP | 0178008 | 4/1986 |
| EP | 0454256 | 10/1991 |
| EP | 0533227 | 3/1993 |
| EP | 0579330 | 5/1996 |
| EP | 0736326 | 9/1996 |
| WO | WO 98/38147 | 9/1998 |
| WO | WO 99/01218 | 1/1999 |
| WO | WO 99/39825 | 8/1999 |
| WO | WO 99/61550 | 12/1999 |

OTHER PUBLICATIONS

Blom et al., Carbon Dioxide Reforming of Methane Over Lanthanum-Modified Catalysts in a Fluidized Bed Reactor, *Catalysis Today*, Dec. 2, 1994, vol. 21, issues 2-3, pp. 534-544.

Shah et al., Design Parameters Estimations for Bubble Column Reactors, Journal Review, *AIChE Journal*, May 1982, vol. 28, pp. 353-379.

* cited by examiner

ATTRITION RESISTANT GAMMA-ALUMINA CATALYST SUPPORT

This application is a continuation of application Ser. No. 09/844,379 filed Apr. 27, 2001, now U.S. Pat. No. 6,740,621 which is a divisional of U.S. patent application Ser. No. 09/316,562, filed May 21, 1999, now U.S. Pat. No. 6,262,132.

The Government of the United States of America has rights to this invention pursuant to Contract No. DE-AC22-92 PC92108 awarded by the U.S. Department of Energy.

BACKGROUND OF THE INVENTION

1. Technical Field

In one aspect, this invention relates to methods of reducing catalyst attrition losses for hydrocarbon synthesis processes conducted in high agitation reaction systems. More particularly, but not by way of limitation, the present invention relates to methods of reducing catalyst attrition losses for hydrocarbon synthesis processes conducted in three-phase reaction systems. In another aspect, this invention relates generally to attrition resistant catalysts for conducting Fischer-Tropsch synthesis.

2. Background

In Fischer-Tropsch processes, synthesis gases comprising carbon oxides and hydrogen are reacted in the presence of Fischer-Tropsch catalysts to produce liquid hydrocarbons. Fischer-Tropsch synthesis processes are most commonly conducted in fixed bed, gas-solid or gas-entrained fluidized bed reaction systems, fixed bed reaction systems being the most commonly used. It is recognized in the art, however, that slurry bubble column reactor systems offer tremendous potential benefits over these commonly used Fischer-Tropsch reaction systems. However, the commercial viability of slurry bubble column processes has been questioned. The unique reaction conditions experienced in slurry bubble column processes are extremely harsh. Thus, catalyst attrition losses in slurry bubble column processes can be both very high and costly. In fact, many of the best performing catalysts employed in other Fischer-Tropsch reaction systems quickly break down when used in slurry bubble column systems.

Heretofore, little has been done to even evaluate or model the harsh conditions experienced in slurry bubble column reactor processors, much less solve the attrition loss problem. Thus, a need presently exists for a means of both (a) reducing catalyst attrition losses and (b) increasing the viability of higher performance catalysts in slurry bubble column processes and in other such "high agitation" reaction systems.

As mentioned above, the synthesis gas, or "syngas," used in Fischer-Tropsch processes is typically a mixture consisting primarily of hydrogen and carbon oxides. Syngas is typically produced, for example, during coal gasification. Processes are also well known for obtaining syngas from other hydrocarbons, including natural gas. U.S. Pat. No. 4,423,265 to Chu et al. notes that the major processes for producing syngas depend either upon the partial combustion of a hydrocarbon fuel with an oxygen-containing gas or the reaction of the fuel with steam, or on a combination of these two reactions. U.S. Pat. No. 5,324,335 to Benham et al., explains the two primary methods (i.e., steam reforming and partial oxidation) for producing syngas from methane. The Encyclopedia of Chemical Technology, Second Edition, Volume 10, pages 3553–433 (1966), Interscience Publishers, New York, N.Y. and Third Edition, Volume 11, pages 410–446 (1980), John Wiley and Sons, New York, N.Y. is said by Chu et al. to contain an excellent summary of gas manufacture, including the manufacture of synthesis gas.

It has long been recognized that syngas can be converted to liquid hydrocarbons by the catalytic hydrogenation of carbon monoxide. The general chemistry of the Fischer-Tropsch synthesis process is as follows:

$$CO + 2H_2 \rightarrow (-CH_2-) + H_2O \qquad (1)$$

$$2CO + H_2 \rightarrow (-CH_2-) + CO_2 \qquad (2)$$

The types and amounts of reaction products, i.e., the lengths of carbon chains, obtained via Fischer-Tropsch synthesis vary dependent upon process kinetics and the catalyst selected.

Many attempts at providing active catalysts for selectively converting syngas to liquid hydrocarbons have previously been disclosed. U.S. Pat. No. 5,248,701 to Soled et al., presents an over-view of relevant prior art. The two most popular types of catalysts heretofore used in Fischer-Tropsch synthesis have been iron-based catalysts and cobalt-based catalysts. U.S. Pat. No. 5,324,335 to Benham et al. discusses the fact that iron-based catalysts, due to their high water gas shift activity, favor the overall reaction shown in (2) above, while cobalt-based catalysts tend to favor reaction scheme (1).

Recent advances have provided a number of catalysts active in Fischer-Tropsch synthesis. Besides iron and cobalt, other Group VIII metals, particularly ruthenium, are known Fischer-Tropsch catalysts. The current practice is to support such catalysts on porous, inorganic refractory oxides. Particularly preferred supports include silica, alumina, silica-alumina, and titania. In addition, other refractory oxides selected from Groups III, IV, V, VI and VIII may be used as catalyst supports.

The prevailing practice is to also add promoters to the supported catalyst. Promoters can include ruthenium (when not used as the primary catalyst component), rhenium, hafnium, cerium, and zirconium. Promoters are known to increase the activity of the catalyst, sometimes rendering the catalyst three to four times as active as its unpromoted counterpart.

Contemporary cobalt catalysts are typically prepared by impregnating the support with the catalytic material. As described in U.S. Pat. No. 5,252,613 to Chang et al., a typical catalyst preparation may involve impregnation, by incipient wetness or other known techniques, of, for example, a cobalt nitrate salt onto a titania, silica or alumina support, optionally followed or preceded by impregnation with a promoter material. Excess liquid is then removed and the catalyst precursor is dried. Following drying, or as a continuation thereof, the catalyst is calcined to convert the salt or compound to its corresponding oxide(s). The oxide is then reduced by treatment with hydrogen, or a hydrogen-containing gas, for a period of time sufficient to substantially reduce the oxide to the elemental or catalytic form of the metal. U.S. Pat. No. 5,498,638 to Long points to U.S. Pat. Nos. 4,673,993, 4,717,702, 4,477,595, 4,663,305, 4,822,824, 5,036,032, 5,140,050, and 5,292,705 as disclosing well known catalyst preparation techniques.

As also mentioned above, Fischer-Tropsch synthesis has heretofore been conducted primarily in fixed bed reactors, gas-solid reactors, and gas-entrained fluidized bed reactors, fixed bed reactors being the most utilized. U.S. Pat. No. 4,670,472 to Dyer et al. provides a bibliography of several references describing these systems. The entire disclosure of U.S. Pat. No. 4,670,472 is incorporated herein by reference.

In contrast to these other hydrocarbon synthesis systems, slurry bubble column reactors are "three phase" (i.e., solid, liquid, and gas/vapor) reaction systems involving the introduction of a fluidizing gas into a reactor containing catalyst particles slurried in a hydrocarbon liquid. The catalyst particles are slurried in the liquid hydrocarbons within a reactor chamber, typically a tall column. Syngas is then introduced at the bottom of the column through a distributor plate, which produces small gas bubbles. The gas bubbles migrate up and through the column, causing beneficial agitation and turbulence, while reacting in the presence of the catalyst to produce liquid and gaseous hydrocarbon products. Gaseous products are captured at the top of the SBCR, while liquid products are recovered through a filter which separates the liquid hydrocarbons from the catalyst fines. U.S. Pat. Nos. 4,684,756, 4,788,222, 5,157,054, 5,348,982, and 5,527,473 reference this type of system and provide citations to pertinent patent and literature art. The entire disclosure of each of these patents is incorporated herein by reference.

It is recognized that conducting Fischer-Tropsch synthesis using a SBCR system could provide significant advantages. As noted by Rice et al. in U.S. Pat. No. 4,788,222, the potential benefits of a slurry process over a fixed bed process include better control of the exothermic heat produced by the Fischer-Tropsch reactions, as well as better maintenance of catalyst activity by allowing continuous recycling, recovery and rejuvenation procedures to be implemented. U.S. Pat. Nos. 5,157,054, 5,348,982, and 5,527,473 also discuss advantages of the SBCR process.

Although the use of slurry bubble column reactors for commercial applications offers significant potential advantages over fixed bed and other types of reactor systems, the viability of the slurry bubble column process has heretofore been questioned, owing in large part to high catalyst attrition losses and costs. As mentioned above, slurry bubble column reactor processes are extremely demanding on catalysts from a physical strength standpoint. Many catalyst formulations lack any practical application in SBCR's because of the rate of physical attrition experienced. In addition to catalyst loss, the physical destruction and attrition of the catalyst results in (a) poorer distribution of the catalyst in the reactor, (b) filtration problems in removing liquid products, and (c) possible contamination of the products with catalytic material.

The significance of the attrition problem was seen, for example, during the Fischer-Tropsch Demonstration Run III conducted in October 1996 at the U.S. Department of Energy's Alternative Fuels Development Unit (a slurry bubble column reactor) in LaPorte, Tex. (See Brown et al., in Paper 27E for AICHEME Meeting in Houston, Mar. 10, 1997). The catalyst selected for that demonstration was a promising, "improved" cobalt catalyst which exhibited high activity in laboratory tests. However, the LaPorte run had to be terminated when the catalyst unexpectedly broke down and seriously plugged the process filters.

As this example also suggests, most of the work performed heretofore in Fischer-Tropsch catalyst development has focused on the activity and/or selectivity of the catalysts, with little or no attention being given to their physical or mechanical properties. Most catalysts have been designed for fixed bed reaction systems, which are much less demanding in terms of attrition resistance than are slurry bubble column reactors.

Recently, U.S. Pat. Nos. 5,648,312, 5,677,257, and 5,710,093 disclosed formulations of hydrogenation catalysts which are said to provide improved attrition resistance. The catalyst supports used in these formulations are substantially spherical particles consisting of substantially homogeneous mixtures of silica particles and silicon carbide particles.

It is known that the use of spheroidal supports in the preparation of supported metal catalysts for fluidized bed applications tends to reduce catalyst attrition. However, the mere use of spherical supports is not sufficient, in and of itself, to obtain acceptable attrition resistance for slurry bubble column applications.

SUMMARY OF THE INVENTION

The present invention satisfies the needs and resolves the problems discussed above. The invention provides a method for reducing catalyst attrition losses in hydrocarbon synthesis processes conducted in high agitation reaction systems, particularly in three-phase reaction systems. As used herein and in the claims, the phrase "high agitation reaction systems" refers to slurry bubble column reactor systems and to other reaction systems wherein catalyst attrition losses, resulting from fragmentation, abrasion, and other similar or related mechanisms, at least approach the attrition losses experienced in slurry bubble column systems.

In one aspect, the inventive method comprises the step of reacting a synthesis gas in a high agitation reaction system in the presence of a catalyst comprising a γ-alumina support, wherein the γ-alumina support includes an amount of titanium or titania effective for increasing the attrition resistance of the catalyst. The titanium or titania will preferably be present in the γ-alumina support in an amount of not less than 800 parts per million (ppm) by weight of titanium.

In another aspect, the inventive method for reducing catalyst attrition losses in hydrocarbon synthesis processes conducted in high agitation reaction systems comprises the step of reacting a synthesis gas in a high agitation reaction system in the presence of a catalyst comprising a γ-alumina support which has been treated, after calcination, with an acidic, aqueous solution. The acidic, aqueous solution will preferably have a pH of not more than 5.

In yet another aspect, the inventive method for reducing catalyst attrition losses in hydrocarbon synthesis processes conducted in high agitation reaction systems comprises the step of reacting a synthesis gas in a high agitation reaction system in the presence of a catalyst comprising cobalt on a γ-alumina support wherein the cobalt is present in an amount in the range of from about 10 parts by weight (pbw) to about 70 pbw, per 100 pbw of the γ-alumina support, and the cobalt has been applied to the γ-alumina support by totally aqueous impregnation using an effective aqueous solution composition, and an effective amount of the aqueous solution, to achieve incipient wetness of the γ-alumina support with the desired amount of cobalt. The aqueous solution preferably has a pH of not more than about 5.

In yet another aspect, the inventive method for reducing catalyst attrition losses in hydrocarbon synthesis processes conducted in high agitation reaction systems comprises the step of reacting a synthesis gas in a high agitation reaction system in the presence of a catalyst wherein the catalyst comprises cobalt on a γ-alumina support and the catalyst further comprises an amount of lanthana promoter effective for increasing the attrition resistance of the catalyst. The amount of cobalt present in the catalyst is preferably in the range of from about 10 pbw to about 70 pbw, per 100 pbw of the γ-alumina support. The amount of lanthana present in the catalyst is preferably in the range of from about 0.5 to about 8 pbw, per 100 pbw of the γ-alumina support.

In yet another aspect, the inventive method for reducing catalyst attrition losses in hydrocarbon synthesis processes conducted in high agitation reaction systems comprises the step of reacting a synthesis gas in a high agitation reaction system in the presence of a catalyst comprising a γ-alumina support, wherein said γ-alumina support is produced from boehmite having a crystallite size, in the 021 plane, in the range of from about 30 to about 55 Ångstroms.

In one preferred embodiment of the inventive method, the high agitation reaction system is a three phase (i.e., solid, liquid, and gas/vapor) reaction system. In a particularly preferred embodiment of the inventive method, the high agitation reaction system is a slurry bubble column reaction system.

The present invention also provides a method of producing an attrition-resistant catalyst. The catalyst produced by the inventive method includes a calcined γ-alumina support. In one aspect, this inventive method comprises the step, after calcination of the support but before adding catalytic materials thereto, of treating the support with an acidic, aqueous solution having an acidity level effective for increasing the attrition resistance of the catalyst. The present invention also provides an attrition resistant catalyst produced by the inventive method.

The present invention further provides a method of producing an attrition-resistant catalyst support. The inventive method for producing an attrition-resistant catalyst support comprises the step of treating calcined γ-alumina with an acidic, aqueous solution having an acidity level effective for increasing the attrition resistance of the calcined alumina. The present invention also provides an attrition-resistant catalyst support produced by the inventive method.

Further objects, features, and advantages of the present invention will be apparent upon examining the accompanying drawings and upon reading the following detailed description of the preferred embodiments.

DETAILED DESCRIPTION OF THE PREFERRED EMBODIMENTS

Catalyst Compositions

The present invention provides supported cobalt catalysts which are well suited for use in Fischer-Tropsch synthesis processes. These catalysts are particularly well suited for use in three-phase reactor processes and other high agitation reaction systems. Examples of general catalyst compositions provided by the present invention include: (a) cobalt, without any promoter, preferably supported on γ-alumina or doped γ-alumina; (b) cobalt, with one or more noble metal promoters, preferably supported on γ-alumina or doped γ-alumina; (c) cobalt, promoted with both a noble metal promoter and one or more selectivity promoters (preferably an alkali or rare earth oxide), preferably supported on γ-alumina or doped γ-alumina; and (d) cobalt, promoted with one or more selectivity promoters and without a noble metal promoter, preferably supported on γ-alumina or doped γ-alumina. Examples of typical promoters include, but are not limited to, noble metals such as ruthenium, metal oxides such as oxides of zirconium, lanthana, or potassium, and other oxides of elements from Groups IA, IIA, IVA, VA, and VIA.

Preferred catalyst compositions comprise (per 100 parts by weight of support): from about 10 to about 70 pbw cobalt; from about 0.1 to about 8 pbw ruthenium (when present); from about 0.1 to about 8 pbw potassium (when present); and from about 0.5 to about 8 pbw lanthana (when present). The catalyst can also include other promoter materials. We have discovered that, to obtain a particularly desirable combination of attrition resistance, selectivity, and activity, particularly in high agitation reaction systems such as slurry bubble column reactors, the catalysts will most preferably comprise (per 100 parts by weight of support): from about 15 to about 55 pbw (more preferably from about 20 to about 45 pbw) cobalt; from about 0.2 to about 1.5 pbw ruthenium (when present); from about 0.2 to about 1.0 pbw potassium (when present); and from about 0.5 to about 5.0 pbw (most preferably from about 0.9 to about 2.5 pbw) lanthana (when present).

The Catalyst Support

Figure 1:
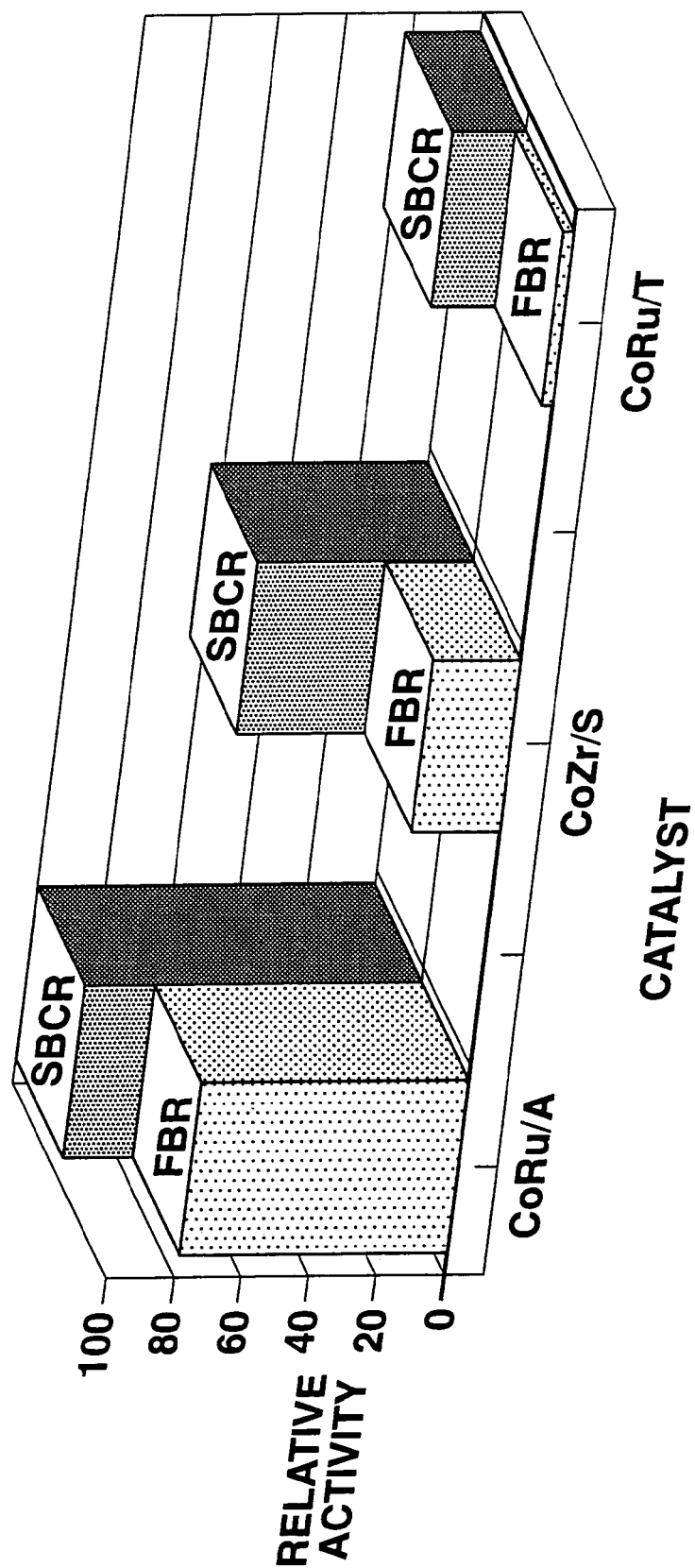
FIG. 1 provides a graph comparing the Fischer-Tropsch synthesis performances in fixed bed and slurry bubble column reactors of promoted cobalt catalysts supported on alumina, silica, and titania.

FIG. 1 shows that, for cobalt catalysts used in both fixed bed and a slurry bubble column reactor systems, the particular support employed plays a major role in influencing the overall hydrocarbon production rate (i.e., catalyst activity) with little or no effect on product selectivity. For the supports tested, catalyst activities ranked in the following order: $Al_2O_3 > SiO_2 >> TiO_2$. With respect to alumina supports, comparisons with literature data and additional tests revealed that the source of the alumina and the pretreatment procedures used also play major roles in determining the performance of the resulting, cobalt-based, Fischer-Tropsch catalysts.

All titania-supported cobalt catalysts tested, with or without promoters, were found to have poor Fischer-Tropsch synthesis properties in both fixed bed and SBCR systems. Compared to γ-alumina and silica, titania supports have much lower surface areas and pore volumes. Thus, they do not readily retain high cobalt loadings.

Although having relatively high surface areas, silica-supported cobalt catalysts showed low Fischer-Tropsch synthesis performance. Silica-supported cobalt catalysts are unstable in reaction conditions, such as those usually encountered in Fischer-Tropsch reaction systems, where a significant amount of water is present. The formation of cobalt-silica compounds under these conditions is believed to cause this lower performance. To prevent or at least slow down silicate formation, the silica surface must typically be coated with oxide promoters, such as $ZrO_2$, prior to cobalt impregnation.

Characteristics and Preparation of Preferred Alumina Supports

The catalyst support employed in the present invention is preferably a γ-alumina support having: a low level of impurities, especially sulfur (preferably less than 100 ppm sulfur); a spheroidal shape; an average particle size in the range of from about 10 to about 150 μm (most preferably from about 20 to about 80 microns); a BET surface area, after calcination, in the range of from about 200 to about 260 $m^2/g$; and a porosity in the range of from about 0.4 to about 1.0 $cm^3/g$.

The alumina support is preferably produced from relatively high purity, synthetic boehmite. As discussed hereinbelow, the boehmite can be formed from aluminum alkoxide of the type obtained in the manufacture of synthetic fatty alcohols. Alternatively, suitable, high purity boehmite materials can be formed from aluminum alkoxide produced by alcohol/aluminum metal reaction processes.

The aluminum alkoxide is preferably hydrolyzed to produce high purity, synthetic, monohydrate alumina. Next, this material is preferably spray-dried to yield highly porous, spherical boehmite particles of relatively high surface area. The particulate boehmite material is preferably then sieved to remove fines and large particles so that a desired particle size range is obtained (most preferably from about 20 to about 80 microns). The sieved material is calcined to convert the boehmite particles to a γ-alumina support material having the desired surface area and porosity. The boehmite material will preferably be calcined at a temperature of at least 350° C. (more preferably from about 400° C. to about 700° C. and most preferably about 500° C.) for a period of from about 3 to about 24 hours (more preferably from about 5 to about 16 hours and most preferably about 10 hours). The desired calcination temperature is preferably reached by slowly heating the system at a rate of about 0.5–2.0° C./minute.

As shown in the examples presented hereinbelow, we have discovered that the attrition resistances of the supported catalyst are unexpectedly improved when the alumina support is formed from a synthetic boehmite having a crystallite size (in the 021 plane) in the range of from about 30 to about 55 Ångstroms, preferably in the range of from about 40 to about 50 Ångstroms. As will be understood by these skilled in the art, the boehmite production process can be readily controlled to obtain desired crystallite sizes within these ranges.

For a given set of calcining conditions, the crystallite size of the boehmite material determines the average pore size, the pore size distribution, and the surface area of the calcined γ-alumina material obtained. As the boehmite crystallite size increases, the surface area of the calcined alumina product decreases and the average pore radius of the calcined alumina product increases. We have discovered that, generally, decreasing the average pore radius of the calcined alumina material increases its attrition resistance.

Examples of commercially-supplied boehmite materials suitable for forming the preferred γ-alumina supports employed in the present invention include the CATAPAL and PURAL aluminas supplied by Condea/Vista. As discussed below, commercial materials of this type are particularly effective when intentionally produced to have certain targeted titanium "impurity" levels. Product quality reports for the CATAPAL aluminas indicate that these products, as presently produced and sold, can have titania impurity levels varying all the way up to 3000 ppm of elemental titanium by weight. The PURAL products, on the other hand, typically have varying titanium impurity levels of up to about 600 ppm.

Titanium Doping of γ-Alumina Supports

As shown hereinbelow, we have discovered that the presence of titanium in the γ-alumina support material unexpectedly and surprisingly improves significantly the attrition resistance of γ-alumina-supported Fischer-Tropsch catalysts used in high agitation reaction systems. The titanium dopant will preferably be present in the γ-alumina support in an amount of at least 800 ppm of titanium by weight. The dopant will more preferably be present in the support in an amount in the range of from about 800 ppm to about 2000 ppm of titanium and will most preferably be present in an amount in the range of from about 1000 to about 2000 ppm. The titanium dopant can be added at substantially any time but will most preferably be added prior to crystallization of the boehmite.

As is well known to those skilled in the art, one method of producing synthetic boehmite materials utilizes aluminum alkoxides recovered as byproducts of certain processes (e.g., the Ziegler Process) employed for manufacturing synthetic fatty alcohols. The Ziegler Process typically comprises the steps of: (1) reacting high purity alumina powder with ethylene and hydrogen to produce aluminum triethyl; (2) polymerizing ethylene by contacting it with the aluminum triethyl, thus resulting in the formation of aluminum alkyls; (3) oxidizing the aluminum alkyls with air to produce aluminum alkoxides; and (4) hydrolizing the aluminum alkoxides to produce alcohols and an alumina byproduct. The oxidation step of the Ziegler process is typically catalyzed by an organic titanium compound which is itself converted to titanium alkoxide. The titanium alkoxide remains with and is co-hydrolized with the aluminum alkoxide, thus resulting in an alumina byproduct which is "doped" with a small amount of titania.

Another process for forming synthetic boehmite utilizes aluminum alkoxide produced by reacting an alcohol with a highly pure aluminum powder. The aluminum alkoxide is hydrolyzed to produce an alcohol, which is recycled for use in the alkoxide formation step, and alumina. Because this process does not involve an oxidation step, the alumina product typically does not contain titanium. However, for purposes of the present invention, any desired amount of titanium dopant can be included in the alumina product by, for example, adding a titanium alkoxide to, and co-hydrolyzing the titanium alkoxide with, the aluminum alkoxide. If desired, the same process can be used to add other dopants such as, for example, silica, lanthanum, or barium.

Heretofore, support manufacturers and catalyst users have simply considered titania, if present in the alumina support, to be a harmless impurity. Of the commercial synthetic boehmite products presently available in the market, some are produced by the Ziegler process, others are produced by the above-described aluminum alkoxide hydrolysis process, and still others are produced by a combination of these processes wherein the resulting products or product precursors are blended together. Such products are sold and used interchangeably, without regard to the small amount, if any, of the titania present.

Thus, the amount of titanium present in commercial γ-alumina supports can vary from 0 ppm to as high as 3000 ppm titanium by weight or more. Titanium concentrations can also vary significantly between different batches of the same commercial product.

Figure 2:
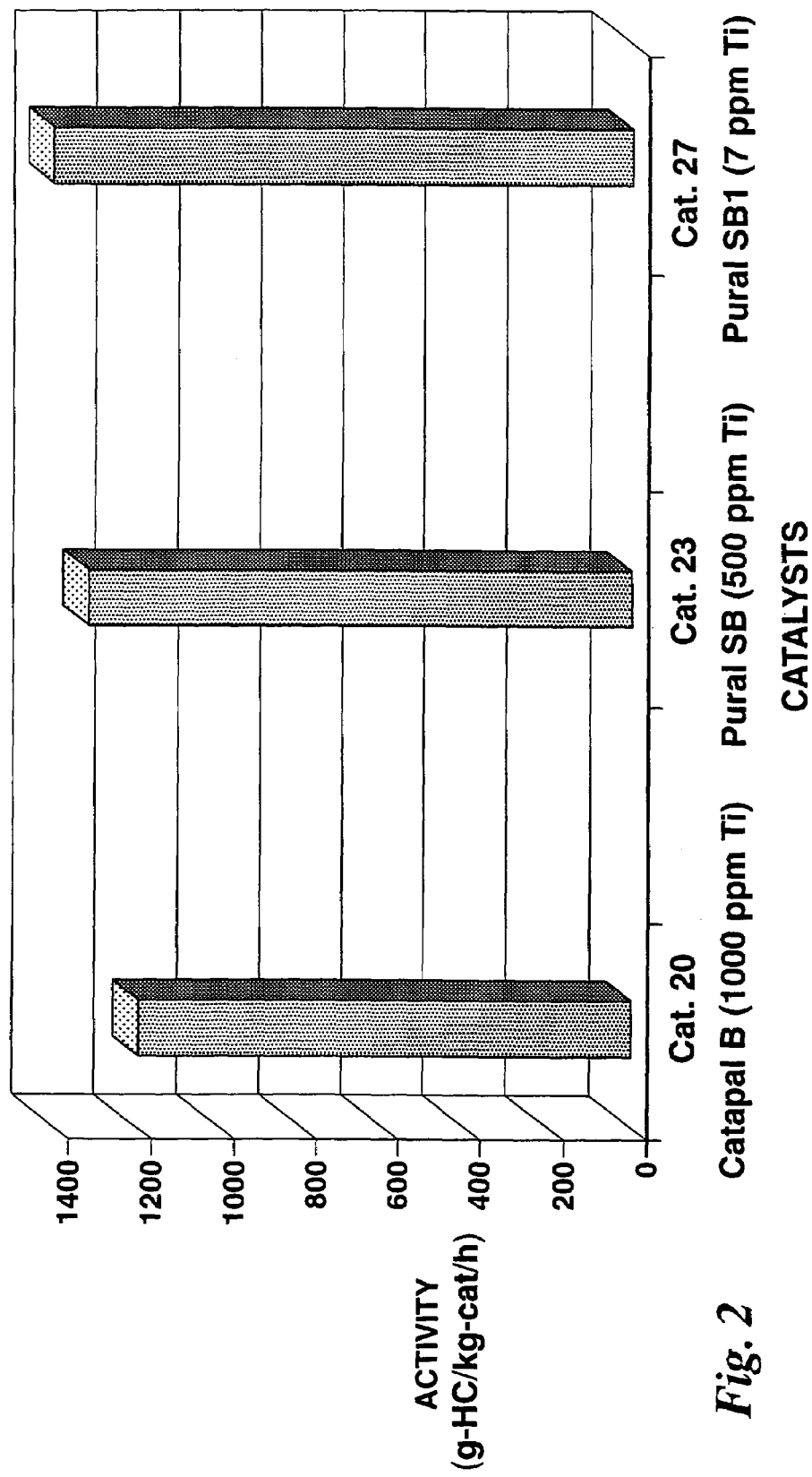
FIG. 2 provides a graph showing the effect of titanium concentration on the activities of ruthenium-promoted, cobalt-on-alumina catalysts.

As mentioned above, because the fixed bed and other reaction systems now commonly used are much less severe, the art has focused primarily on improving the activity and/or selectivity of Fischer-Tropsch catalysts. FIG. 2 illustrates the detrimental effect of titania on the activities of ruthenium promoted, cobalt-on-alumina catalysts. FIG. 2 shows the activities (g-HC/kg-cat/hr) of three catalysts (catalysts 20, 23, and 24) which were produced and tested as described hereinbelow in Example 7. Catalysts 20, 23, and 24 were identical in all respects except that catalyst 24 was formed on a γ-alumina support found to have a titania concentration, expressed as titanium, of about 7 ppm by weight, catalyst 23 was formed on a γ-alumina support found to have a titanium concentration of about 500 ppm, and catalyst 20 was formed on a γ-alumina support found to have a titanium concentration of about 1000 ppm. FIG. 2 shows that, as the amount of titania in the support increased, the activity of the catalyst declined from about 1340 for catalyst 24, to about 1322 for catalyst 23, and to about 1112 for catalyst 20. Thus, any preference in the art as to the presence of titanium would heretofore have been that no titania dopant be included in the γ-alumina support.

We have discovered, however, that the intentional inclusion of controlled amounts of titanium in γ-alumina supports unexpectedly and surprisingly reduces catalyst attrition losses in high agitation reaction systems to such a degree as to greatly outweigh any incidental reduction in catalyst activity. The improvement provided by our discovery is particularly effective for addressing the uniquely harsh conditions experienced in slurry bubble column and other three-phase reaction systems. In fact, this discovery could be said to actually increase the catalyst activities obtainable in high agitation reaction systems by now allowing certain "higher performance" catalysts to be used in these systems.

Catalyst Preparation

The catalytic components of the preferred catalysts are preferably added to the support by totally aqueous impregnation using appropriate aqueous solution compositions and volumes to achieve incipient wetness of the support material with the desired metal loading(s). Promoted catalysts are most preferably prepared by totally aqueous co-impregnation. Examples of typical promoters include, but are not limited to: noble metals; metal oxides such as oxides of Zr, La, K; and other oxides of elements from Groups IA, IIA, IVA, VA, and VIA.

In accordance with the present invention, the totally aqueous impregnation of cobalt onto the support, with or without one or more desired promoters, is preferably accomplished by the steps of: (a) calcining the alumina support in the manner described above; (b) impregnating the support with an aqueous solution of cobalt nitrate, or of cobalt nitrate and one or more promoter compounds (preferably one or more promoter-nitrates [e.g., ruthenium (III) nitrosyl nitrate] and/or promoter-chlorides [e.g., ruthenium III chloride], most preferably promoter-nitrates) using a sufficient quantity of the solution to achieve incipient wetness with a desired loading of cobalt and of any desired promoter(s); (c) drying the resulting catalyst precursor for about 5–24 hours at approximately 80–130° C., with moderate mixing, to remove solvent water and obtain a dried catalyst; and (d) calcining the dried catalyst in air or nitrogen by slowly raising the temperature of the system at a rate of about 0.5–2.0° C. per minute to approximately 250–400° C. and then holding for at least 2 hours to obtain the oxide form of the catalyst. Multiple impregnation/coimpregnation steps (b) can be used when higher cobalt loadings are desired.

The preferred cobalt nitrate concentrations employed for aqueous impregnation and aqueous co-impregnation typically provide pH values in the 1–3 range. As shown hereinbelow, pH values within this range unexpectedly and surprisingly provide a significant improvement in attrition resistance.

As one example, a particularly preferred ruthenium-promoted cobalt catalyst is prepared according to the following procedure. First, the support, preferably γ-alumina, is calcined at from about 400° C. to about 700° C., preferably about 500° C., for about 10 hours. The calcined support is then impregnated with an aqueous solution containing both cobalt nitrate [$Co(NO_3)_2$-$6H_2O$] and ruthenium (III) nitrosyl nitrate [$Ru(NO)(NO_3)_3$-$xH_2O$] using an appropriate quantity to achieve incipient wetness with the desired loadings of cobalt and ruthenium. The resulting catalyst precursor is then dried for 5 hours at 115° C. with moderate stirring in order to remove the solvent water. The dried catalyst is then calcined in air by raising its temperature at a rate of 1° C./min to 300° C. and holding for at least 2 hours.

In another example, a doubly promoted cobalt catalyst can be prepared in a similar fashion using a second promoter nitrate (e.g., potassium nitrate [$KNO_3$] or lanthanum nitrate [$La(NO_3)_3$.$H_2O$]) dissolved in the same solution which contains the cobalt and ruthenium compounds.

Acceptable ruthenium salts, such as those used in the present invention, have very limited aqueous solubilities. These salts are only moderately soluble in cold water and, when heated in an effort to increase solubility, tend to decompose and precipitate. However, by using the aqueous co-impregnation method of the present invention, superior ruthenium-promoted catalysts having the desired concentration ranges cited above can be produced without difficulty.

Until recently, ruthenium-promoted cobalt catalysts were typically prepared by coprecipitation of the metal components onto the support material. Such methods typically do not yield well dispersed systems, and therefore result in an inefficient use of the active metals. Coprecipitation methods generally also involve the use of two solutions, the first containing the support material and the dissolved promoter salt(s) and the second containing a precipitating agent (e.g., potassium carbonate). The solutions must be employed in relatively large quantities, typically several orders of magnitude larger than used in incipient wetness impregnation.

Due to the shortcomings of coprecipitation processes, impregnation techniques have become the preferred means of putting cobalt and its promoters onto porous supports. However, whenever ruthenium has been used as a promoter, the impregnation methods have employed an organic ruthenium precursor dissolved in an organic solvent. This use of organic solvents as the impregnating media for ruthenium promoters has, of course, resulted from the poor aqueous solubility characteristics of the practical ruthenium salts. Incipient wetness impregnation utilizes a relatively minute amount of impregnation solution. The amount of solution employed is typically only an amount sufficient to fill the pores of the support material. However, the promoter salt(s) must be completely dissolved in this small amount of solution.

When an organic impregnation method is used, the drying step involves the evaporation of the organic solvent, which requires some environmentally acceptable way of disposing of the solvent vapor. In addition, special explosion proof equipment for catalyst drying and calcining is required. The need for such equipment and procedures adds greatly to the cost of the catalyst.

In contrast, the preferred method employed in the present invention for producing ruthenium-promoted and other promoted cobalt catalysts utilizes a totally aqueous co-impregnation technique, followed by drying and calcination of the resulting catalyst precursor. For noble metals, the promoter-metal is preferably either a promoter-nitrate, (e.g., ruthenium (III) nitrosyl nitrate) or a promoter-chloride (e.g., ruthenium (III) chloride).

We have discovered that, when aqueous co-impregnation solutions are used comprising the amounts of cobalt nitrate and ruthenium nitrate (or chloride) desired for the present invention, the ruthenium salt(s) will, unexpectedly, dissolve in the small amount of solution employed. Moreover, the ruthenium salts dissolve without the addition of acids or other agents and without heating. Although the reason for this result is unknown, it is believed that the acidity imparted to the solution by the cobalt nitrate may be at least partially responsible.

Acidic Aqueous Impregnation and/or Pretreatment of Support

As shown hereinbelow, the attrition resistances of γ-alumina supports and of the catalysts produced therefrom are also unexpectedly improved by (a) utilizing an acidic aqueous impregnation solution and/or (b) pretreating the catalyst support (preferably after calcination and before addition of the catalytic components) with an acidic aqueous solution. In each case, the aqueous solution must have an acidity level effective for increasing attrition resistance. The aqueous cobalt impregnation and coimpregnation solutions employed in the present invention typically have pH values within this range. However, nitric acid can be used, for example, to adjust the pH of the impregnation solution, if necessary, or to form an appropriate pretreatment solution.

Catalyst Activation

To provide optimum performance, it is presently preferred that the catalyst be activated/reduced in a hydrogen-containing gas by slowly increasing the temperature of the catalyst, preferably at a rate of about 0.5–2.0° C./minute, to approximately 250–400° C. (preferably about 350° C.) and holding at the desired temperature for at least 2 hours. After reduction, the catalyst is preferably cooled in flowing nitrogen.

The reducing gas preferably comprises from about 1% to 100% by volume hydrogen, with the remainder (if any) being an inert gas, typically nitrogen. The reducing gas is preferably delivered at a rate of about 2–4 (preferably about 3) liters per hour per gram of catalyst. The reduction procedure is preferably conducted in a fluidized bed reactor. The reduction procedure is most preferably conducted at conditions (i.e., temperature, flow rate, hydrogen concentration, etc.) effective to ensure that a very low water vapor partial pressure is maintained during the procedure.

The Fischer-Tropsch Reaction Process

The catalysts prepared and activated in accordance with the present invention can be employed in generally any Fischer-Tropsch synthesis process. For slurry bubble column and other three-phase reaction systems, the catalyst will preferably be slurried in a Fischer-Tropsch wax or in a synthetic fluid (e.g., a $C_{30}$ to $C_{50}$ range isoparaffin polyalphaolefin such as that available from Chevron under the name SYNFLUID) having properties similar to those of Fischer-Tropsch wax. The catalyst slurry will preferably have a catalyst concentration in the range of from about 5% to about 40% by weight based on the total weight of the slurry.

The synthesis gas feed used in the reaction process will preferably have a $CO:H_2$ volume ratio of from about 0.5 to about 3.0 and will preferably have an inert gas (i.e., nitrogen, argon, or other inert gas) concentration in the range of from 0 to about 60% by volume based on the total volume of the feed. The inert gas is preferably nitrogen.

Prior to initiating the reaction process, the activated catalyst will most preferably be maintained in an inert atmosphere. Before adding the catalyst thereto, the slurry fluid will preferably be purged with nitrogen or other inert gas to remove any dissolved oxygen. The slurry composition will also preferably be transferred to the reaction system under an inert atmosphere.

A particularly preferred SBCR reaction procedure comprises the steps of: (a) filling the SBCR, under an inert atmosphere, with the activated catalyst slurry; (b) heating and pressurizing the SBCR, under an inert atmosphere, to the desired pretreatment conditions (preferably a temperature in the range of from about 220° C. to about 250° C. and a pressure in the range of from about 50 to about 500 psig); (c) replacing the inert gas with hydrogen and holding the system at these conditions for from about 2 to about 20 hours; (d) purging the system with inert gas and lowering the reaction system temperature, if necessary, to a point at least about 10° C. below the desired reaction temperature; (e) carefully replacing the inert gas with the desired synthesis gas; and (f) heating and pressurizing the reaction system, as necessary, to a desired operating temperature, preferably in the range of from about 190° C. to about 300° C., and a desired operating pressure, preferably in the range of from about 50 to about 900 psig.

EXAMPLES

In the following Examples, actual laboratory SBCR runs and two other independent testing techniques, the Jet Cup test and the ultrasonic test, were used, as indicated, to determine and characterize the attrition resistance properties of various catalysts. The Jet Cup and ultrasonic techniques were found to simulate the attrition mechanisms which occur in slurry bubble column reactors (i.e., fragmentation, abrasion, etc.).

Figure 3:
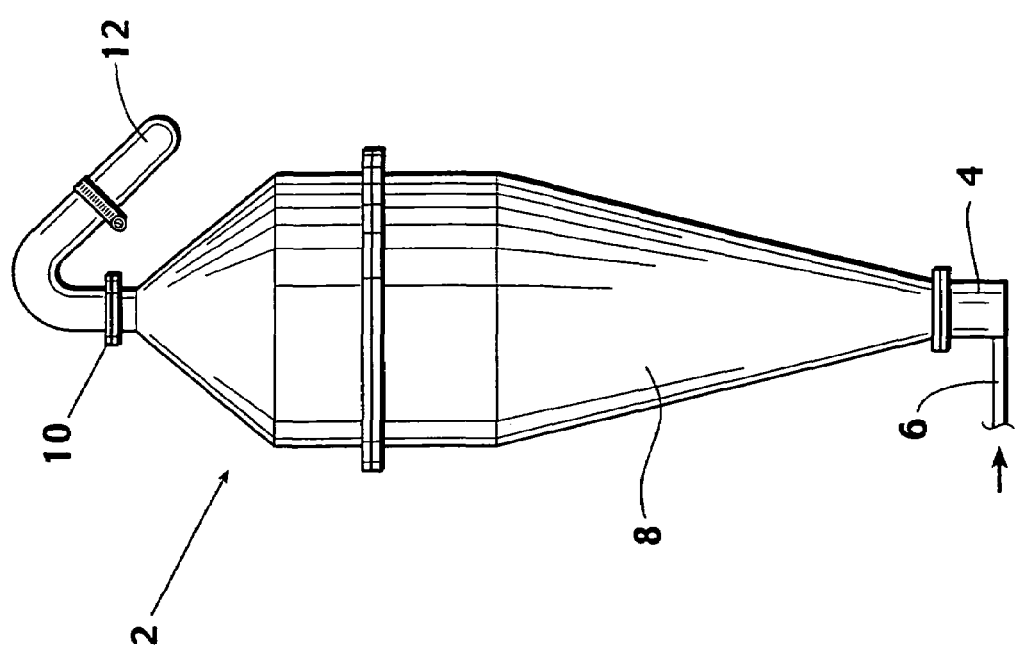
FIG. 3 provides a schematic diagram of a Jet Cup system used for conducting attrition resistance tests.

A Jet Cup system 2 is illustrated in FIG. 3. The system comprises: a sample cup 4; an air inlet tube 6, connected to the bottom of the sample cup; a settling chamber 8; and a fines collection assembly 10 including a collection thimble 12. Before each test, the fines collection assembly was weighed and its mass recorded. Five grams of sample were placed in the sample cup and the sample cup was then attached to the settling chamber. After all joints were sealed, humidified air (relative humidity of 60±5%) was passed at a controlled flow rate through the system for one hour.

The humidified air was introduced tangentially into the sample cup at the bottom of the assembly and flowed out of the system through the thimble. The thimble was a cellulose filter which operated to retain fines carried out of the settling chamber by the air stream. In order not to interrupt the air flow during the test, two collection thimbles were alternately used, with one thimble being quickly replaced by the other and weighed at 5 minutes, 15 minutes, and then 30 minutes into the test. At the end of one hour, the air flow was stopped and the fines in the thimbles, and also the coarse particles collected in the Jet Cup, were recovered and analyzed.

Figure 4:
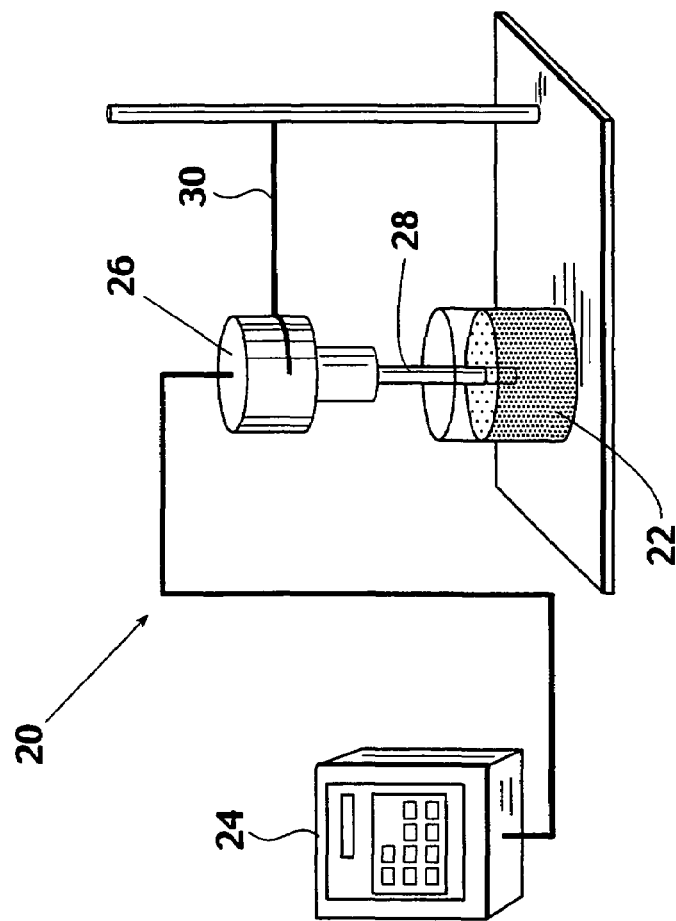
FIG. 4 provides a schematic diagram of an ultrasonic system used for conducting attrition resistance tests.

An ultrasonic test system 20 is illustrated in FIG. 4. The system comprises: a container 22; a 20 kHz Tekmar TM501 Sonic Disrupter 24 equipped with a CV26 horn 26 and a 0.5 inch tip 28; and a horn support frame 30. In each test, a pre-weighed sample was dispersed in 400 ml of distilled water by stirring. Each suspension had a solids concentration of about 2.5 vol %. The suspensions were treated for 15 minutes at a Sonic Disrupter setting of 350 watts. Because temperature is reported to be a factor affecting ultrasonic energy output, a water bath was used to keep the suspension temperatures relatively constant. At the end of each run, the slurry was transferred and sampled and then characterized using a particle size analyzer. The remainder of the slurry was filtered and then dried in an oven at 110° C. for sieving or for particle size analysis.

The system used for characterizing the particulate samples generated in the SBCR, Jet Cup, and ultrasonic tests, as well as the starting materials used, was a Leeds & Northrup Microtrac laser particle size analyzer model 7990-11. Each SBCR and Jet Cup test sample was prepared for analysis by pre-mixing the sample, placing the pre-mixed sample in 50 ml of deionized water, and then dispersing the particulate sample material using an ultrasonic bath. Each of the resulting sample suspensions had a particulate concentration of approximately 2.5 vol %.

After each ultrasonic test, the test suspension was stirred and portions were drawn from the top, center and bottom of the suspension. These individual portions were then analyzed in the particle size analyzer and the portion results were averaged.

Example 1

Attrition resistance is defined in this Example as the percent reduction in particle size based on mean volumetric diameter, as measured using a Microtrac particle size analyzer, after an approximately 240 hour run in a slurry bubble column reactor (SBCR). The attrition resistances of a number of catalysts were compared. A series of 7 catalysts, varying significantly with respect to the supports, preparation methods, and additives used, were selected for this purpose. The catalyst formulations tested were as follows:

CATALYST 1: (Non-promoted, γ-alumina-supported catalyst with 13 wt % Cobalt.)

Preparation Procedure:

CATAPAL B alumina from Condea/Vista in the boehmite form was calcined at 500° C. for 10 hours to convert it to γ-alumina. It was then presieved to 400–0 mesh (i.e., a particle size of greater than 38 microns). The γ-alumina was then impregnated with an aqueous solution of Co nitrate [$Co(NO_3)_2.6H_2O$], using an appropriate quantity to achieve incipient wetness (ca. 1.2 ml/g) with the desired loading of Co. The resulting catalyst precursor was then dried in air at 115° C. for 12 hours and calcined in air at 300° C. for 2 hours (with a heating rate of ca. 1° C./min to 300° C.).

Reduction Procedure Before Reaction:

The catalyst was reduced in 3000 cc/g/hr of pure hydrogen flow by heating at 1° C./min to 350° C. and holding for 10 hours.

CATALYST 2: (γ-alumina-supported cobalt catalyst with 20 wt % cobalt, 0.43 wt % ruthenium and 1 wt % lanthana.)

Preparation Procedure:

CATAPAL B alumina in the boehmite form was calcined at 600° C. for 10 hours to convert it to γ-alumina. It was then presieved to 400–0 mesh and impregnated in two steps. In the first step, the γ-alumina was impregnated with an aqueous solution of cobalt nitrate [$Co(NO_3)_2.6H_2O$], using an appropriate quantity to achieve incipient wetness (ca. 1.2 ml/g) with the desired loading of cobalt. The resulting catalyst precursor was dried in air at 120° C. for 16 hours and calcined in air at 300° C. for 2 hours (with a heating rate of ca. 1° C./min to 300° C.). In the second step, the catalyst precursor was impregnated with an aqueous solution of lanthanum nitrate hexahydrate and ruthenium nitrosyl nitrate using an appropriate quantity to achieve incipient wetness with the desired loading of Ru and $La_2O_3$. The resulting catalyst precursor was dried in air at 120° C. for 12 hours and then prereduced in pure hydrogen at a flow rate of 720 cc/g/hr by the sequential steps of (a) heating the impregnated catalyst to 100° C. at a rate of 1° C./min and then maintaining the catalyst at 100° C. for 1 hr, (b) heating the catalyst to 200° C. at a rate of 1° C./min and holding at 200° C. for 2 hours, and then (c) heating at a rate of 10° C./min to 360° C. and holding for 16 hours. Finally, the catalyst was cooled below 200° C., purged with nitrogen, and cooled further. Air was bled into the nitrogen stream for 16 hours at a rate of ca. 1 cc air per 50 cc nitrogen per minute per 5 g of catalyst.

Reduction Procedure Before Reaction: Same as Catalyst 1.

CATALYST 3: (γ-alumina-supported cobalt catalyst with 20 wt % cobalt, 0.5 wt % ruthenium and 0.3 wt % potassium.)

Preparation Procedure:

Same as Catalyst 1 with the addition of ruthenium nitrosyl nitrate and potassium nitrate in the cobalt nitrate solution used for impregnation.

Reduction Procedure Before Reaction: Same as Catalyst 1.

CATALYST 4: (γ-alumina-supported cobalt catalyst with 20 wt % cobalt, 5 wt % copper, and 4 wt % chromium.)

Preparation Procedure:

CATAPAL B alumina in the boehmite form was calcined at 500° C. for 10 hours to convert it to γ-alumina. It was then presieved to 400–0 mesh and impregnated with an aqueous solution of copper nitrate [$Cu(NO_3)_2.xH_2O$], and chromium nitrate [$Cr(NO_3)_3.9H_2O$], using an appropriate quantity to achieve incipient wetness (ca. 1.2 ml/g) with the desired loading of Cu and Cr. The resulting precursor was then dried in air at 110° C. for 16 hours and calcined in air at 750° C. for 24 hours (with a heating rate of ca. 1° C./min to 750° C.). Next, the calcined precursor was impregnated with an aqueous solution of cobalt nitrate [$Co(NO_3)_2.6H_2O$] using an appropriate quantity to achieve incipient wetness with the desired loading of Co. The precursor was then dried in air at 115° C. for 12 hours and calcined in air at 300° C. for 2 hours (with a heating rate of ca. 1° C./min to 300° C.).

Reduction Procedure Before Reaction: Same as Catalyst 1.

CATALYST 5: (Non-promoted, silica-supported catalyst with 20 wt % cobalt.)

Preparation Procedure:

The silica support (DAVISON Grade 952) was calcined at 500° C. for 10 hours. It was then presieved to 400–250 mesh (i.e., a particle size of 38–63 microns). A mixture comprised of the support and an aqueous solution of cobalt nitrate [$Co(NO_3)_2.6H_2O$] was kneaded for 3.5 hours. The amount of the aqueous solution used was 110% of the pore volume of the silica support. The resulting catalyst precursor was next dried in air for 5 hours at 115° C. with moderate stirring and then calcined in air at 300° C. for 2 hours (with a heating rate of ca. 1° C./min to 300° C.).

Reduction Procedure Before Reaction:

The catalyst was reduced in 3000 cc/g/hr of pure hydrogen flow by heating at 1° C./min to 250° C. and holding for 10 hours.

CATALYST 6: (Zirconium-promoted, silica-supported catalyst with 20 wt % cobalt and 8.5 wt % zirconium.)

Preparation Procedure:

The silica support (DAVISON Grade 952) was calcined at 500° C. for 10 hours. It was then presieved to 400–0 mesh and impregnated with an aqueous solution of zirconium oxonitrate [$ZrO(NO_3)_2$] using an appropriate quantity to achieve incipient wetness with the desired loading of Zr. The Zr-loaded $SiO_2$ was then dried in an oven for 5 hours at 115° C. with moderate stirring and calcined in air at 300° C. for 2 hours (with a heating rate of ca. 1° C./min to 300° C.). The calcined, Zr-loaded silica was next impregnated with an aqueous solution of cobalt nitrate [$Co(NO_3)_2.6H_2O$] using an appropriate quantity to achieve incipient wetness with the desired loading of Co. The drying and calcination processes were then repeated.

Reduction Procedure Before Reaction: Same as Catalyst 5.

CATALYST 7: (Zirconium-promoted, silica-supported catalyst with 20 wt % cobalt, 8.5 wt % zirconium, 0.5 wt % Ru and 0.3 wt % K.)

Preparation Procedure:

Same as Catalyst 6 with the addition of ruthenium nitrosyl nitrate and potassium nitrate to the cobalt nitrate solution used in the second impregnation step.

Reduction Procedure Before Reaction: Same as Catalyst 5.

The catalytic properties for Fischer-Tropsch synthesis in a slurry bubble column reactor, as well as the attrition properties, of catalysts 1–7 are shown in Table 1. These examples indicate that attrition resistance can vary significantly based upon the particular supports, preparation methods, and additives used. Based on 64 SBCR runs with a wide variety of cobalt catalysts, including the above-described catalysts 1–7, having differing formulations and using either spherical alumina or spherical silica supports, the average particle size reductions for each category of support were as follows:

| All Al$_2$O$_3$-supported Co catalysts | 8.4% |
|---|---|
| All SiO$_2$-supported Co catalysts | 13.7% |

TABLE 1

SBCR Reaction and Attrition Results For Catalysts 1–7

| Catalyst No. | Support | Additives | Activity (g-HC/g-cat./h) | Selectivity % CH$_4$ | Selectivity α | Average Particle Size, (μm) | Particle Size Reduction (%) |
|---|---|---|---|---|---|---|---|
| Catalyst 1 | Al$_2$O$_3$ | — | 1.07 | 10.9 | 0.85 | 85.6 | 8.4 |
| Catalyst 2 | Al$_2$O$_3$ | La, Ru | 1.31 | — | 0.81 | 67.7 | 4.3 |
| Catalyst 3 | Al$_2$O$_3$ | Ru, K | 1.22 | 7.3 | 0.86 | 72.8 | 1.6 |
| Catalyst 4 | Al$_2$O$_3$ | Cu, Cr | 0.23 | 10.9 | 0.78 | 79.5 | 4.3 |
| Catalyst 5 | SiO$_2$ | — | 0.67 | 7.6 | 0.83 | 107.1 | 12.2 |
| Catalyst 6 | SiO$_2$ | Zr | 1.24 | 10.7 | 0.82 | 87.2 | 10.2 |
| Catalyst 7 | SiO$_2$ | Ru, Zr, K | 0.90 | 9.9 | 0.88 | 82.4 | 14.2 |

The particle size is reported as the mean volume diameter as measured by a Microtrac particle size analyzer.
The particle size reduction was estimated from Microtrac measurements carried out before and after reaction (ca. 220–250 hours-on-stream)
Reaction Conditions: Catalyst weight: ca. 15 g, screened thru 150 × 400 mesh, calcined and reduced externally, T = 240° C., P = 450 psi, H$_2$/CO ratio = 2, Total flow rate: ca. 15 L/min, Diluent: N$_2$: ca.60%

Example 2

Figure 5:
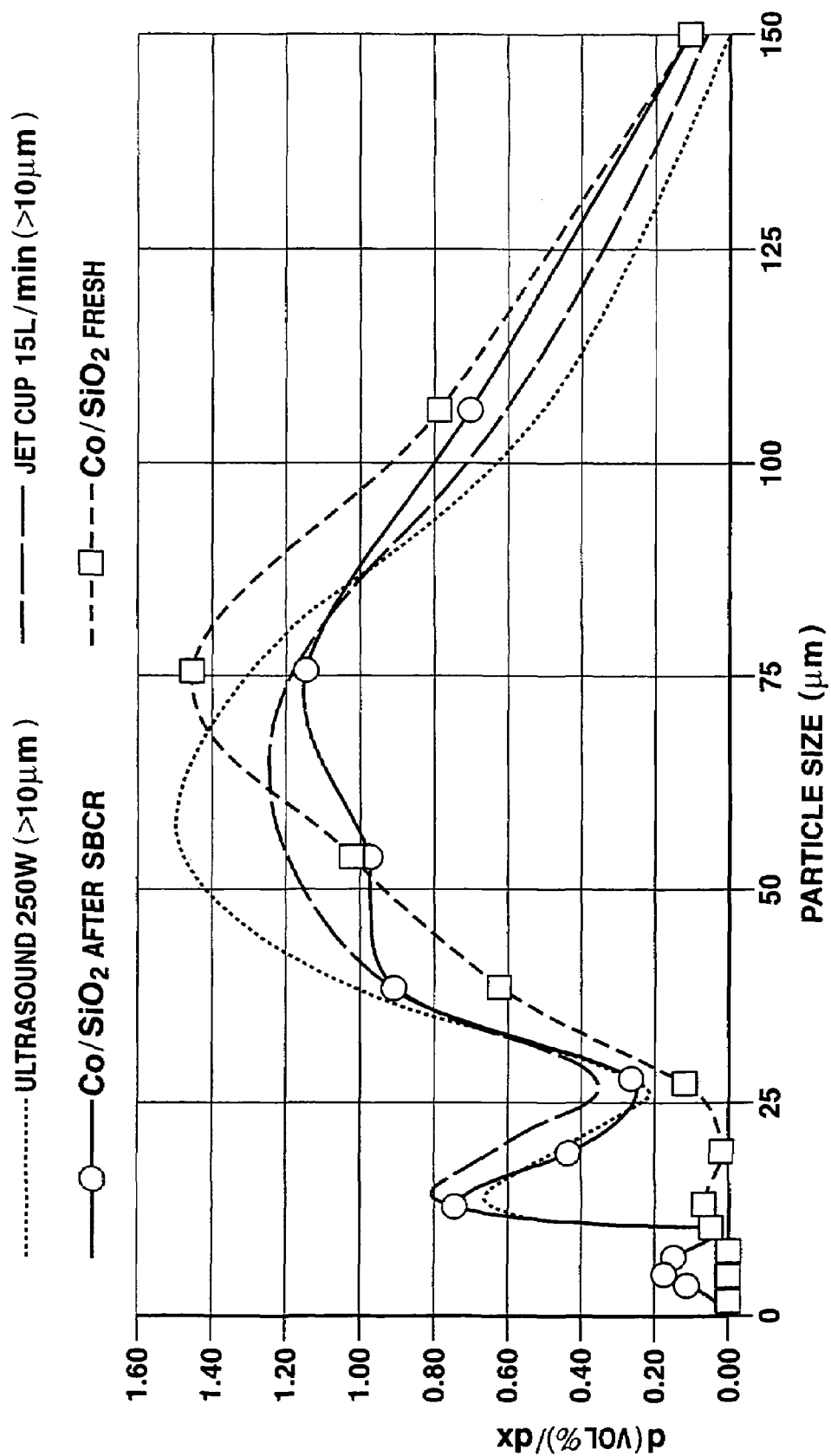
FIG. 5 provides a graph comparing the particle size distributions of silica-supported cobalt catalysts before and after SBCR, Jet Cup and ultrasound attrition tests.

Comparison of Attrition Results Obtained from Jet Cup, Ultrasound and SBCR Tests A silica supported catalyst (Catalyst 5 in Example 1) which had shown relatively low attrition resistance based upon the percent reduction in mean diameter after an approximately 240 hour SBCR run was used to gauge the effectiveness and accuracy of the Jet Cup and ultrasonic testing techniques. The Jet Cup and ultrasonic tests were conducted in the manner described above. FIG. 5 provides a comparison of the particle size distributions of the silica supported cobalt catalyst before and after (a) a SBCR run, (b) a Jet Cup test, and (c) an ultrasound attrition test. As indicated in FIG. 5, the distributions obtained after the 20 minute ultrasound test and the one hour Jet Cup test compared remarkably well with the particle size distribution obtained after a 240 hour SBCR run.

Example 3

Comparison of Alumina, Silica, and Titania Supports

Various supports, with and without cobalt loading, were tested using the above-described ultrasound and Jet Cup procedures. Prior to testing, the bare supports were calcined and presieved to 400–0 mesh in accordance with substantially the same procedures used in preparing the corresponding cobalt catalysts. The catalysts used for these tests were as follows:

CATALYST 8: (γ-alumina-supported cobalt catalyst with 20 wt % cobalt, 0.43 wt % ruthenium, and 1 wt % lanthana.)

Preparation Procedure:
Same as Catalyst 2 except that the second impregnation step was carried out with an acetone/ethanol (2:1) solution of lanthanum nitrate hexahydrate and ruthenium acetylacetonate. The amount of solution used was ca. 2 ml/g.

The solvent was removed at 0.01 atm and 25–30° C. in a rotary evaporator and the catalyst precursor was dried at 90° C. with moderate stirring. The precursor was then prereduced and passivated in accordance with the same procedures employed for Catalyst 2.

Reduction Procedure Before Reaction: Same as Catalyst 2

CATALYST 9: (Zirconium-promoted, γ-alumina-supported catalyst with 20 wt % cobalt and 8.5 wt % zirconium.)

Preparation Procedure:
Same as Catalyst 1 with the addition of zirconium oxonitrate in the cobalt nitrate solution used for impregnation.

Reduction Procedure Before Reaction: Same as Catalyst 1.
CATALYST 10: (Non-promoted, silica supported catalyst with 20 wt % cobalt.)

Preparation Procedure:
Same as Catalyst 5 except for the use of incipient wetness impregnation rather than kneading with an excess volume of solution.

Reduction Procedure Before Reaction: Same as Catalyst 5.
CATALYST 11: (Zirconium-promoted, silica supported catalyst with 20 wt % cobalt and 8.5 wt % zirconium.)

Preparation Procedure:
Same as Catalyst 5 with the addition of zirconium oxonitrate in the cobalt nitrate solution used for impregnation.

Reduction Procedure Before Reaction: Same as Catalyst 5.
CATALYST 12: (Zirconium-promoted, silica-supported catalyst with 20 wt % cobalt and 8.5 wt % zirconium.)

Preparation Procedure:
Same as Catalyst 11 with the addition of zirconium oxonitrate in a separate incipient wetness impregnation step after cobalt impregnation by the kneading method. The catalyst precursor was dried and calcined after the zirconium impregnation step by the same procedures as used after the cobalt impregnation step.

Reduction Procedure Before Reaction: Same as Catalyst 5.
CATALYST 13: (Non-promoted, titania-supported cobalt catalyst with 20 wt % cobalt.)

Preparation Procedure:
Anatase titania (DEGUSSA P25) was wetted to incipient wetness with distilled water and then dried in an oven at 60°

C. with moderate stirring. It was next calcined at 650° C. for 16 hours resulting in a ca. 97% rutile support. The calcined titania was presieved to 400-0 mesh and then impregnated with an acetone solution of cobalt nitrate [$Co(NO_3)_2 \cdot 6H_2O$] using an appropriate quantity of solution to obtain a slurry with the desired loading of cobalt. Next, the resulting catalyst precursor was dried in a rotor evaporator at 25° C. and dried under a vacuum at 140° C. for 16 hours. The precursor was then further calcined in air at 250° C. for 3 hours. Finally, the dried catalyst was rescreened to remove fines.

Reduction Procedure Before Reaction:

The catalyst was reduced in 1000 cc/g/hr of pure hydrogen by heating to 350° C. and holding for 16 hours.

CATALYST 14: (Non-promoted, titania-supported cobalt catalyst with 20 wt % cobalt.)

Preparation Procedure

Anatase titania was wetted to incipient wetness with distilled water and then dried in an oven at 60° C. with moderate stirring. It was next calcined at 350° C. for 16 hours to produce a support having primarily an anatase structure. Next, the calcined titania was presieved to 400-0 mesh and then impregnated in 2 steps. In the first step, the support was impregnated with an aqueous solution of cobalt nitrate [$Co(NO_3)_2 \cdot 6H_2O$] using an appropriate quantity to achieve incipient wetness with 60% of the desired final loading of cobalt. This catalyst precursor was dried in an oven for 5 hours at 115° C. with moderate stirring. The dried precursor was then calcined in air by raising its temperature at a heating rate of ca. 1° C./min to 250° C. and holding for 3 hours. In the second impregnation step, the remaining 40% of the cobalt was applied in the same manner. The same drying and calcination procedures used in step one were then repeated and the catalyst was rescreened to remove fines.

Reduction Procedure Before Reaction: Same as Catalyst 13

CATALYST 15: (Non-promoted, titania-supported cobalt catalyst with 12 wt % cobalt.)

Preparation Procedure:

Same as Catalyst 13, except that a cobalt loading of 12 wt % was formed rather than 20 wt %.

Reduction Procedure Before Reaction: Same as Catalyst 13.

The attrition test results for catalysts 8–15 are shown in Table 2. The results are presented in terms of the percentage of fines (particles less than 16 microns) as measured by Microtrac analysis. The attrition resistance results show that, prior to cobalt impregnation, titania was the most attrition resistant support material, followed by alumina and with silica trailing far behind. In contrast, however, a comparison of the results obtained for the cobalt catalysts produced using these same supports shows that the γ-alumina-supported catalysts surprisingly had the highest attrition resistances.

TABLE 2

Attrition Resistances of Alumina, Silica, and Titania Supports With and Without Cobalt Loading (Ultrasound and Jet Cup Results)

| Catalyst (Support/ Additives) | Before Attrition Test | Fines (<16 μm) (%) After Ultrasound | After Jet Cup |
|---|---|---|---|
| CATAPAL B Alumina | 0.9 | 7.0 | 10.8 |
| Catalyst 8 ($Al_2O_3$/Co, La, Ru) | 0.7 | 3.6 | 1.9 |
| Catalyst 9 ($Al_2O_3$/Co, Zr) | 0.8 | 6.1 | 5.9 |
| DAVISON Silica 952 Grade | 4.7 | 24.8 | 29.2 |
| Catalyst 10 ($SiO_2$/Co) | 0 | 8.1 | 18.6 |
| Catalyst 11 ($SiO_2$/Co, Zr) | 0 | 5.5 | 8.6 |
| Catalyst 12 ($SiO_2$/Co, Zr) | 0 | 8.5 | 15.6 |
| Titania DEGUSSA P25 | 0 | 12 | 2.4 |
| Catalyst 13 ($TiO_2$/Co) | 0.9 | 11.4 | 13.8 |
| Catalyst 14 ($TiO_2$-Anatase/Co) | 0.8 | 54.3 | 34.6 |
| Catalyst 15 ($TiO_2$-Rutile/Co) | 4.1 | 10.8 | 19.6 |

Example 4

Effect of Preparation Method on the Attrition Resistance of Cobalt Catalysts having γ-Alumina Supports The effects of various preparation methods, especially organic and aqueous methods of impregnation, on attrition resistance were determined using a series of SBCR runs. Each run lasted about 240 hours. The same alumina support, CATAPAL B manufactured by Condea/Vista, was used for all the catalysts. The catalysts also contained identical amounts of ruthenium and lanthana. The formulations of those catalysts tested but not already described were as follows:

CATALYST 16: (γ-alumina-supported, cobalt catalyst with 20 wt % cobalt, 0.5 wt % ruthenium, and 1 wt % lanthana.)

Preparation Procedure:

CATAPAL B alumina in the boehmite form was calcined at 750° C. for 16 hours to convert it to γ-alumina. It was then presieved to 400-0 mesh and impregnated in three steps (40%, 30%, and 30%)., each step utilizing an acetone solution of cobalt nitrate [$Co(NO_3)_2 \cdot 6H_2O$], ruthenium acetylacetonate, and lanthanum nitrate [$La(NO_3)_3 \cdot H_2O$] in an appropriate quantity to achieve incipient wetness (ca. 1 ml/g) with the desired loadings of cobalt, ruthenium, and lanthanum. Following each step, the catalyst precursor was dried in a rotor evaporator at 40° C. for at least 30 minutes and calcined in air at 300° C. for 2 hours.

The impregnated catalyst was then prereduced in 720 cc/g/hr of pure hydrogen. The catalyst was first heated to 100° C. at the rate of 1° C./min and held for 1 hour. Next, the catalyst was heated to 200° C. at a rate of 1° C./min and held for 2 hours. The catalyst was then heated at 10° C./min to a temperature of 360° C. and held for 16 hours. Finally, the catalyst was cooled to below 200° C., purged with nitrogen, and cooled further. Air was added to the nitrogen stream for 16 hours at ca. 1 cc air per 50 cc nitrogen per minute per 5 g of catalyst.

Reduction Procedure Before Reaction: Same as Catalyst 8.

CATALYST 17: (γ-alumina-supported cobalt catalyst with 20 wt % cobalt, 0.43 wt % ruthenium, and 1 wt % lanthana.)

Preparation Procedure: Same as Catalyst 8.

Reduction Procedure Before Reaction: Same as Catalyst 8.

CATALYST 18: (γ-alumina-supported cobalt catalyst with 20 wt % cobalt, 0.43 wt % ruthenium, and 1 wt % lanthana.)

Preparation Procedure: Same as Catalyst 8, but using entirely aqueous impregnation.

Reduction Procedure Before Reaction: Same as Catalyst 8.

CATALYST 19: (γ-alumina-supported cobalt catalyst with 20 wt % cobalt, 0.43 wt % ruthenium, and 1 wt % lanthana.)

Preparation Procedure:

CATAPAL B alumina in the boehmite form was calcined at 750° C. for 16 hours to convert it to γ-alumina. It was then presieved to 400–0 mesh and impregnated with an aqueous solution of cobalt nitrate [$Co(NO_3)_2 \cdot 6H_2O$] and ruthenium (III) nitrosyl nitrate [$Ru(NO)(NO_3)_3 \cdot xH_2O$] and lanthanum nitrate [$La(NO_3)_3 H_2O$] using an appropriate quantity to achieve incipient wetness (ca. 1 ml/g) with the desired loadings of cobalt, ruthenium and lanthanum. The catalyst precursor was then dried in air at 120° C. for 12 hours.

Pre-reduction Procedure:

The catalyst was then prereduced in 720 cc/g/hr of pure hydrogen. The catalyst was first heated to 100° C. at a rate of 1° C./min and held for 2 hours. The catalyst was then heated at 10° C./min to a temperature of 360° C. and held for 16 hours. Finally, the catalyst was cooled to below 200° C., purged with nitrogen, and cooled further. Air was added to the nitrogen stream at ca. 1 cc air per 50 cc nitrogen per minute per 5 g of catalyst for 16 hours.

Reduction Procedure Before Reaction: Same as Catalyst 2.

The reaction and attrition results obtained with these catalysts and with catalysts 2 and 8 are presented in Table 3. The catalysts listed in Table 3 had identical or substantially identical compositions, but were prepared by different methods. Table 3 shows that the catalysts prepared by totally aqueous impregnation unexpectedly and surprisingly had higher attrition resistances than did the cobalt catalysts prepared by other methods.

TABLE 3

Effect of Aqueous vs. Non-Aqueous Preparation Methods on $Co/Al_2O_3$ Attrition Resistance

| Catalyst No. | Support | Additives | Activity (g-HC/g-cat./h) | Selectivity % $CH_4$ | α | Average Particle Size, (μm) | Particle Size Reduction (%) |
|---|---|---|---|---|---|---|---|
| 8* | $Al_2O_3$ | La, Ru | 1.42 | 12.5 | 0.80 | 73.6 | 8.1 |
| 8* | $Al_2O_3$ | La, Ru | — | — | — | 73.6 | 10.0 |
| 8* | $Al_2O_3$ | La, Ru | 1.32 | 22.9 | 0.77 | 73.6 | 3.3 |
| 16* | $Al_2O_3$ | La, Ru | 1.53 | 16.7 | 0.88 | 76.8 | 5.5 |
| 17* | $Al_2O_3$ | La, Ru | 1.64 | 15.3 | 0.79 | 70.1 | 14.4 |
| 17* | $Al_2O_3$ | La, Ru | 1.80 | 15.2 | 0.89 | 81.4 | 10.4 |
| 18# | $Al_2O_3$ | La, Ru | 1.37 | 12.7 | 0.80 | 75.6 | 1.3 |
| 2# | $Al_2O_3$ | La, Ru | — | — | — | 64.6 | 0.3 |
| 2# | $Al_2O_3$ | La, Ru | 1.31 | 8.3 | 0.81 | 67.7 | 4.3 |
| 19# | $Al_2O_3$ | La, Ru | 1.32 | 11.2 | 0.80 | 73.1 | 4.4 |

*Catalysts preparation utilizing at least one organic impregnation step
Catalysts preparation utilizing totally aqueous impregnation
The particle size is reported as the mean volume diameter as measured by a Microtrac particle size analyzer.
The particle size reduction was estimated from Microtrac measurements carried out before and after reaction (c.a. 220–250 hours-on-stream)
Reaction Conditions: Catalyst weight: ca. 15 g, screened thru 150 × 400 mesh, calcined and reduced externally, T = 240° C., P = 450 psi, $H_2$/CO ratio = 2, Total flow rate: ca. 15 L/min, Diluent: $N_2$: ca.60%

Example 5

Effect of Lanthana Promotion on the Attrition Resistance of Cobalt Catalysts

We have also discovered that the attrition resistances of the cobalt catalysts are unexpectedly and surprisingly enhanced by the addition of a lanthana ($La_2O_3$) promoter. The improved attrition resistance provided by the addition of $La_2O_3$ is not detrimental to Fischer-Tropsch activity, or to Fischer-Tropsch selectivity. Preferred lanthana concentration ranges are provided hereinabove.

The following attrition resistance results were obtained from 47 slurry bubble column reactor runs using a wide variety of cobalt-on-alumina catalysts, including the above-described alumina-supported catalysts described in examples 1–4, having differing formulations. The results are expressed as the percent reduction in particle size of the catalysts based on the difference in mean volumetric diameters of the catalysts as measured, using a Microtrac particle size analyzer, both before reaction in a slurry bubble column reactor and then after runs of approximately 250 hours. The average particle size reductions for catalysts with and without lanthana were as follows:

| | Attrition Resistance (Ave. Particle Size Reduction) |
|---|---|
| All $Al_2O_3$-supported Co catalysts with $La_2O_3$ | 6.6% |
| All $Al_2O_3$-supported Co catalysts with $La_2O_3$ prepared using an aqueous impregnation method | 5.2% |
| All $Al_2O_3$-supported Co catalysts without $La_2O_3$ | 9.2% |

Example 6

Effect of Solution pH on the Attrition Resistance of Alumina Supports

In this example, CATAPAL B alumina samples calcined at 500° C. were treated with aqueous solutions having pH values ranging from 1.0 to 12.5. Acidic solutions were prepared using nitric acid in distilled water. Basic solutions were prepared using ammonium hydroxide in distilled water. After being subjected to incipient wetness treatment with an acidic, neutral, or basic solution for 10 hours, each sample was dried overnight at 120° C. and calcined again at 350° C. for two hours to remove nitrate or ammonium ions. The treated samples were then resieved to ensure that the particle size distribution of each sample was from 45 to 90 microns.

The resulting aluminas were subjected to Jet Cup testing to determine their attrition resistances. The results of the tests, as measured by Microtrac analysis, are presented in Table 5. The results surprisingly revealed that the most attrition resistant γ-aluminas were those treated with the low pH solutions, particularly those solutions having pH values of 5 or less (preferably 3 or less and most preferably from about 3 to about 1).

As already mentioned, the preferred cobalt nitrate concentrations employed for aqueous impregnation and aqueous co-impregnation typically provide particularly desirable pH values in the 1–3 range.

CATALYST 20: (Ru-promoted, cobalt catalyst on CATAPAL B alumina with 20 wt % cobalt and 0.5 wt % ruthenium.)

Preparation Procedure:

CATAPAL B alumina in the boehmite form was calcined at 500° C. for 10 hours to convert it to γ-alumina. It was then presieved to 400-170 mesh (i.e., a particle size of greater than 38 microns and lower than 88 microns) and impregnated with an aqueous solution of cobalt nitrate [$Co(NO_3)_2 \cdot 6H_2O$] and ruthenium (III) nitrosyl nitrate [$Ru(NO)(NO_3)_3 \cdot xH_2O$] using an appropriate quantity to achieve incipient wetness (ca. 1.2 ml/g) with the desired loading of Co and Ru. The catalyst precursor was then dried in air at 115° C. for 5 hours and calcined in air at 300° C. for 2 hours (with a heating rate of ca. 1° C./min to 300° C.).

Reduction Procedure Before Reaction:

The catalyst was reduced in 3000 cc/g/hr of pure hydrogen by heating at 1° C./min to 350° C. and holding for 10 hours.

Each of the following catalysts 21–23 was prepared in the same manner as catalyst 20. The specific supports employed in catalysts 21–23 were as follows:

CATALYST 21: CATAPAL A support supplied by Condea/Vista and produced in substantially the same manner as CATAPAL B.

TABLE 4

Effect of pH on the Attrition Resistance of γ-Alumina (Jet Cup Results)

| Solution pH Value | Mean Volume Diameter* | | 50% Passing Size* | | % Fines# (<11 μm) | |
|---|---|---|---|---|---|---|
| | | % Decrease | | % Decrease | | |
| | As Prepared (μm) | after Jet Cup Test | As Prepared (μm) | after Jet Cup Test | As Prepared | After Jet Cup Test |
| 1.0 | 71.9 | 27.3 | 69.5 | 25.3 | 0 | 4.5 |
| 3.0 | 72.7 | 29.4 | 70.3 | 26.7 | 0 | 6.6 |
| 5.0 | 73.5 | 31.7 | 71.1 | 27.7 | 0 | 6.7 |
| 7.0 | 72.8 | 32.8 | 70.3 | 29.9 | 0 | 8.1 |
| 10.0 | 71.0 | 35.6 | 68.5 | 31.8 | 0 | 10.5 |
| 12.5 | 72.5 | 35.3 | 69.8 | 31.5 | 0 | 10.1 |

Note:
*Error = ±0.8;
= ±0.3

Example 7

Effect of Different Aluminas on the Catalytic Properties and Attrition Resistances of Cobalt-based, Fischer Tropsch Catalysts The effect on attrition resistance and catalytic properties of the type of alumina used was examined using a series of catalysts which, except for the particular alumina supports employed, had the same formulations. Each of the alumina supports was manufactured by Condea/Vista. In each case, the alumina was calcined at 500° C. for 10 hours. All catalysts were prepared by incipient wetness impregnation and contained 20 wt % cobalt and 0.5 wt % ruthenium. The catalysts were prepared as follows:

CATALYST 22: CATAPAL D support supplied by Condea/Vista and produced in substantially the same manner as CATAPAL B.

CATALYST 23: PURAL SB support supplied by Condea/Vista. The PURAL SB was produced by Condea/Vista in the same manner as CATAPAL B, but at a different plant.

The particular CATAPAL A, B, and D support materials employed in catalysts 20–22 were each determined to contain an amount of titania "impurity" of about 1000 ppm by weight (expressed as ppm by weight of titanium) which was incidentally added, as part of the Ziegler Process, prior to the crystallization of the boehmite. In contrast, the particular PURAL SB support material employed in catalyst 23 had been formed by a blending process and was found to contain only about 500 ppm of titania. All of the supports employed in catalyst 20–23 were spherical, γ-alumina supports.

The CATAPAL A, CATAPAL B, and CATAPAL D materials were boehmites having slightly different crystallite sizes. The crystallite sizes for these materials expressed in Ångstroms as determined by X-ray diffraction analysis, were as follows:

|  | CATAPAL | | |
| --- | --- | --- | --- |
|  | A | B | D |
| 020 plane | 26 | 30 | 47 |
| 021 plane | 41 | 43 | 72 |

The crystallite sizes of the CATAPAL A and the CATAPAL B were relatively close. Thus, one would expect their physical properties to be similar. Moreover, the crystallite characteristics of the PURAL SB support were substantially identical to those of the CATAPAL B.

CATALYST 24: (Ru-promoted, cobalt catalyst on γ-alumina with 20 wt % cobalt and 0.5 wt % ruthenium): The support, PURAL SB1, was supplied by Condea/Vista and was identical to PURAL SB except that the PURAL SB 1 support was not doped with titanium.

Preparation and Reduction Procedures: Same as catalyst 20.

The particular γ-alumina support, PURAL SB1, employed in catalyst 24 was specially produced for us by Condea/Vista. The PURAL SB1 was identical to PURAL SB except that special efforts were made to prevent the addition of titanium. An elemental analysis showed that the PURAL SB1 support contained only 7 ppm of titanium.

Catalysts 20–24 were tested in a slurry bubble column reactor. Table 5A shows the average activity and selectivity exhibited by each catalyst over its first 24 hours of use. The same reaction conditions were used in all of the SBCR runs (i.e., 230° C., 450 psig, and 900 l/hr of syngas and nitrogen with nitrogen comprising ca. 60% of the total feed gas).

TABLE 5A

Activity and Selectivity of Co/Al$_2$O$_3$: Effect of Different Aluminas

| CATALYST (Alumina Support) | CATALYST WEIGHT (g) | CO CONV. (%) | ACTIVITY (g/kg-cat/hr) | SELECTIVITIES (% C) | |
| --- | --- | --- | --- | --- | --- |
| | | | | CH$_4$ | C$_5$+ |
| Catalyst 20 (CATAPAL B) | 15.3 | 21.8 | 1112.2 | 8.2 | 82.2 |
| Catalyst 21 (CATAPAL A) | 27.4 | 44.6 | 1257.9 | 10.4 | 79.0 |
| Catalyst 22 (CATAPAL D) | 27.5 | 44.2 | 1261.9 | 10.9 | 79.0 |
| Catalyst 23 (PURAL SB) | 21.5 | 36.3 | 1322.4 | 8.5 | 81.9 |
| Catalyst 24 (PURAL SB1) | 15.1 | 27.1 | 1340.0 | 8.4 | 80.5 |

The attrition resistances of the bare alumina supports used in catalysts 20–24, prior to cobalt impregnation, were examined using the ultrasound and the Jet Cup tests. The results obtained, as determined by Microtrac analysis, are shown in Tables 5B and 5C. Overall, the test results indicate that, although all of the supports were γ-aluminas, the alumina supports having the higher titanium loadings exhibited noticeably better attrition resistance. A comparison of the results obtained for the CATAPAL A, B, and D supports further shows that improved attrition resistance is obtained through the use of boehmites having crystallite characteristics closer to those of the CATAPAL A and CATAPAL B materials.

TABLE 5B

Attrition Resistances of Different γ-Aluminas (Results Before and After Ultrasound Attrition Test)

| | Fines (<11 μm) (%) | |
| --- | --- | --- |
| Alumina | Before | After |
| CATAPAL A | 0.3 | 0.5 |
| CATAPAL B | 0.0 | 4.3 |
| CATAPAL D | 0.4 | 7.8 |
| PURAL SB | 3.2 | 9.8 |

TABLE 5C

Attrition Resistances of Different Aluminas (Results Before and After Jet Cup Attrition Test)

| | Fines (<11 μm) (%)* | |
| --- | --- | --- |
| Alumina | Before | After |
| CATAPAL B | 0 | 7.1 |
| CATAPAL A | 0 | 7.6 |
| CATAPAL D | 0.4 | 7.7 |
| PURAL SB | 2.8 | 17.6 |
| PURAL SB1 | 0 | 10.3 |

*Error = ±0.3

The attrition resistances of promoted cobalt catalysts 20–24 are shown in Tables 5D (ultrasonic results) and 5E (Jet Cup results). These tests reveal that, for all the aluminas used, the impregnation of cobalt significantly improved the attrition results obtained. Further, the catalysts supported on the aluminas having higher titanium loadings had superior attrition resistance.

TABLE 5D

Effect of Different Aluminas on the Attrition Resistance of Cobalt Catalysts (Results Before and After Ultrasound Test)

| | Fines (<11 μm) (%) | |
| --- | --- | --- |
| Catalyst (Alumina Support) | Before | After |
| Catalyst 20 (CATAPAL B) | 0 | 1.0 |
| Catalyst 21 (CATAPAL A) | 0.3 | 0.8 |
| Catalyst 22 (CATAPAL D) | 1.5 | 1.8 |
| Catalyst 23 (PURAL SB) | 2.2 | 4.8 |

TABLE 5E

Effect of Different Aluminas on the Attrition Resistance of Cobalt Catalysts (Results Before and After Jet Cup Test)

| | Fines (<11 μm) (%) | |
| --- | --- | --- |
| Catalyst (Alumina Support) | Before | After |
| Catalyst 20 | 0 | 0.7 |

TABLE 5E-continued

Effect of Different Aluminas on the Attrition Resistance of Cobalt Catalysts (Results Before and After Jet Cup Test)

| Catalyst (Alumina Support) | Fines (<11 μm) (%) Before | After |
|---|---|---|
| (CATAPAL B) Catalyst 21 | 0 | 1.0 |
| (CATAPAL A) Catalyst 22 | 0 | 2.9 |
| (CATAPAL D) Catalyst 23 | 0.4 | 10.5 |
| (PURAL SB) Catalyst 24 | 0 | 5.2 |
| (PURAL SB1) | | |

These tests unexpectedly demonstrate that the presence of titanium in γ-alumina supports, particularly in an amount of more than 800 ppm by weight, or from about 800 ppm to about 2000 ppm, more preferably at least about 1000 ppm and most preferably from about 1000 ppm to about 2000 ppm, significantly improves the attrition resistance of the cobalt catalysts produced therefrom. Except for differences in titanium content, the CATAPAL B and PURAL supports employed in this Example were all produced in the same manner. Additionally, the CATAPAL and PURAL supports were produced by the same manufacturer and were calcined in the same manner. Moreover, the ruthenium-promoted cobalt catalysts formed therefrom were identically produced, calcined, and reduced.

Example 8

Effect of Cobalt Loading on Catalyst Attrition Resistance

Since it was found that cobalt impregnation of γ-alumina significantly improves attrition resistance, the effect of cobalt loading was investigated. A CATAPAL B alumina support which was determined to have a titanium loading of about 1000 ppm, and which was found to have relatively high attrition resistance, especially when impregnated with cobalt, was selected for all the catalysts used in this example. Four different cobalt loadings were tested. The specific formulations of these catalysts were as follows:

CATALYST 25: (Ru-promoted, cobalt catalyst on CATAPAL B alumina with 15 wt % cobalt and 0.4 wt % ruthenium.)

Preparation Procedure:

Same as Catalyst 20, but with only 15 wt % cobalt and 0.4 wt % ruthenium.

CATALYST 26: (Ru-promoted, cobalt catalyst on CATAPAL B alumina with 30 wt % cobalt and 0.8 wt % ruthenium.)

Preparation Procedure:
Same as Catalyst 20, but with 30 wt % cobalt and 0.8 wt % ruthenium. The impregnation was accomplished in two steps using first a solution containing 60% and then a second solution containing the remaining 40% of the required metal precursors. The second step was carried out after drying and calcining the partially loaded catalyst precursor. The drying and calcining steps were then repeated after the second impregnation.

CATALYST 27: (Ru-promoted, cobalt catalyst on CATAPAL B alumina with 40 wt % cobalt and 1.0 wt % ruthenium.)

Preparation Procedure:

Same as Catalyst 26, but with 40 wt % cobalt and 1.0 wt % ruthenium and using three impregnation steps. The three impregnation steps applied 40%, 30%, and then 30% of the metal precursors. Each step was followed by drying and calcining.

The attrition resistances of these catalysts, and of Catalyst 20, are compared in Table 6. Table 6 also shows the activities of these catalysts as measured in a slurry bubble column reactor at 230° C. and 450 psig. These results indicate that attrition resistance and activity increased with increasing cobalt loadings up to 30 wt %.

TABLE 6

Effect of Cobalt Loading on Attrition Resistance (Jet Cup Test)

| Catalyst | Cobalt Loading (wt %) | Activity (g-HC/g-cat/hr) | Attrition Resistance % Fines (<11 μm) After Jet Cup |
|---|---|---|---|
| Catalyst 25 | 15 | 1.157 | 2.7 |
| Catalyst 20 | 20 | 1.240 | 0.8 |
| Catalyst 26 | 30 | 1.666 | 0.3 |
| Catalyst 27 | 40 | 1.505 | 0.4 |

Thus, the present invention is well adapted to carry out the objects and attain the ends and advantages mentioned above, as well as those inherent therein. While the invention has been described with a certain degree of particularity, it is manifest that many changes may be made without departing from the spirit and scope of this disclosure. It is understood that the invention is not limited to the embodiments set forth herein for purposes of exemplification.

The invention claimed is:

1. A γ-alumina catalyst support material having improved attrition resistance produced by a method comprising the steps of:
   (a) treating a particulate γ-alumina material with an acidic aqueous solution comprising water and nitric acid and having a pH of not more than 5 and then
   (b) after step (a) and prior to adding any catalytic material to said particulate γ-alumina material, calcining said particulate γ-alumina material at about 350° C.

2. The γ-alumina catalyst support material of claim 1 wherein said acidic aqueous solution used in step (a) consists essentially of said water and said nitric acid and has a pH in the range of from about 3 to about 1.

3. The γ-alumina catalyst support material of claim 1 wherein said method further comprises the step, after step (a) and prior to step (b), of drying said particulate γ-alumina material.

4. The γ-alumina catalyst support material of claim 3 wherein said particulate γ-alumina material is dried in said step of drying at a temperature of about 120° C.

5. The γ-alumina catalyst support material of claim 1 wherein said acidic aqueous solution used in step (a) consists essentially of said water and said nitric acid.

* * * * *